(12) United States Patent
Hudson et al.

(10) Patent No.: US 6,706,051 B2
(45) Date of Patent: Mar. 16, 2004

(54) HEMOSTATIC SYSTEM FOR BODY CAVITIES

(75) Inventors: John Overton Hudson, Glenfield (GB); Alberto Bauer, Marbella/Malaga (ES)

(73) Assignee: BHK Holding, Ltd., Grand Cayman (KY)

( * ) Notice: Subject to any disclaimer, the term of this patent is extended or adjusted under 35 U.S.C. 154(b) by 244 days.

(21) Appl. No.: 09/927,864

(22) Filed: Aug. 10, 2001

(65) Prior Publication Data

US 2002/0058960 A1 May 16, 2002

Related U.S. Application Data

(63) Continuation-in-part of application No. 09/406,166, filed on Sep. 27, 1999, now Pat. No. 6,306,154, which is a continuation-in-part of application No. 09/057,414, filed on Apr. 8, 1998, now abandoned.

(51) Int. Cl.$^7$ .............................................. A61M 29/00
(52) U.S. Cl. ...................................................... 606/196
(58) Field of Search ................................ 606/196, 192, 606/194, 195, 200; 604/96.01

(56) References Cited

U.S. PATENT DOCUMENTS

| | | |
|---|---|---|
| 4,364,392 A | 12/1982 | Strother et al. |
| 4,638,803 A | 1/1987 | Rand |
| 4,686,962 A | 8/1987 | Haber ........................ 600/30 |
| 4,832,680 A | 5/1989 | Haber et al. .................. 600/31 |
| 5,061,274 A | 10/1991 | Kensey |
| 5,100,385 A | 3/1992 | Bromander ................... 604/99 |
| 5,176,692 A | 1/1993 | Wilkk et al. |
| 5,312,435 A | 5/1994 | Nash et al. |
| 5,486,195 A | 1/1996 | Myers et al. ................ 606/213 |
| 5,545,176 A | 8/1996 | Murtfeldt ..................... 606/192 |
| 5,645,566 A | 7/1997 | Brenneman et al. ......... 606/213 |

FOREIGN PATENT DOCUMENTS

| | | |
|---|---|---|
| EP | 0 252 607 | 5/1987 |
| WO | WO 92/05740 | 4/1992 |
| WO | WO 93/16658 | 9/1993 |
| WO | WO 95/20916 | 8/1995 |
| WO | WO 97/22372 | 6/1997 |

OTHER PUBLICATIONS

"Hi–Lo Tracheal Tube", Mallinckrodt, pp. 1–2, 1998–2001.
"General Features of an Endotracheal Tube", pp. 1–3, Aug. 15, 2001.
Nellcor, "Low Pressure Cuffed Tracheostomy Tubes", pp. 1–2.
Portex, Tracheal Tubes, pp. 1–2.

*Primary Examiner*—Michael J. Milano
*Assistant Examiner*—(Jackie) Tan-Uyen T. Ho
(74) *Attorney, Agent, or Firm*—RatnerPrestia

(57) ABSTRACT

Bleeding is controlled on an inner surface of a body cavity, including a non-vascular body passageway, by inserting into the cavity an expandable balloon which is covered by a hemostatic shroud, expanding the balloon, and compressing the shroud against the site of bleeding. The shroud may be released from the balloon. Subsequently, the balloon may be withdrawn from the body cavity, leaving the shroud in vivo to perform its hemostatic function. Optionally, the shroud can be withdrawn at some later point by the use of an extension "tail" which is included on the shroud. An alternative method of this invention for controlling or preventing a bleeding situation within a pathological cavity is the use of filling material to plug the cavity. The invention also includes the corresponding devices and systems for such control of bleeding within a body cavity or passageway.

41 Claims, 19 Drawing Sheets

HEMOSTATIC SYSTEM FOR BODY CAVITIES

This application is a continuation-in-part of U.S. patent application Ser. No. 09/406,166 filed Sep. 27, 1999 now U.S. Pat. No. 6,306,154, which in turn is a continuation-in-part of U.S. patent application Ser. No. 09/057,414, filed on Apr. 8, 1998 now abandoned.

TECHNICAL FIELD

This invention relates generally to medical devices and methods of use, and more specifically, to materials, apparatus, and methods for facilitating hemostasis within a body cavity or passageway.

BACKGROUND OF THE INVENTION

Nasal passageways, for example, are often susceptible to uncontrolled bleeding caused by various forms of trauma, disease or cellular dysfunction. Methods and devices for controlling, limiting or stopping such bleeding would be useful in a variety of situations, ranging from emergency room care to long term care.

Treatment of intestinal diverticular disease would also be facilitated by methods and devices for the prevention and control of bleeding in such diverticula. However, diverticula present a problem in many cases even if they have not advanced to the stage where they bleed. Diverticula are sacral pockets or protrusions in the intestinal tract, derived from the intestinal lumen and of varying sizes, occurring normally through a defect in the muscular coating of the tract.

As shown in FIG. 17, the diverticula of the colon are usually multiple and may be accompanied by inflammation. In the absence of inflammation, the condition is known as diverticulosis, while in the presence of inflammation, the condition is referred to as diverticulitis. Although the distinction between the two conditions is clear when a colon is examined surgically or histologically, the symptoms of colonic dysfunction due to diverticulosis sometimes mimic those of diverticulitis and, therefore, the clinical distinction between the two conditions may often be blurred. Consequently, diverticular disease of the colon typically refers to all stages of the disease from diverticulosis.

Typically, globular diverticula communicate with the bowel lumen via a narrow neck through which gas can pass freely. They are prone to filling with fecal material extruded through the lumen that may then become firm. Such a process usually begins in the Sigmoid area of the colon and then typically spreads proximally throughout the intestinal tract over the course of several years. Infection and inflammation occurs in approximately 15–25% of patients with diverticulosis.

Complications associated with diverticular disease include sepsis, fistula, bleeding, obstruction, obstruction, and intractable painful disturbance of the bowel function, with typical septic complications being abscess and perforation accompanied with diffuse bacterial and/or feculent peritonitis. One of the most dangerous complications of diverticular disease is that of bleeding diverticula.

Diverticula usually form at a site where an artery supplying blood to mucosa penetrates the muscular wall of the colon. The penetration of the muscular wall causes a "weak point" and a diverticulum may form, with the result that the artery terminates in the mucosa inside the diverticulum. If the diverticulum becomes infected, or if compacted fecal matter causes an irritation, then the end of the artery may fail causing excessive bleeding. As this bleeding is arterial, it is generally very difficult to control, and major surgery involving the forming of a colostomy and a later (few months) reconnecting the colon or removing a section of the colon is often the only available treatment.

Hemostatic agents, such as carboxymethyl cellulose (CMC) and woven knit or matted fabrics thereof, are known for use in the control of bleeding, such as post-trauma and post-surgical bleeding. CMC is defined as a polycarboxylmethyl ether of cellulose or the sodium salt thereof. It is sometimes referred to as cellulose ether, carboxymethylcellulose, or sodium caramellose.

SUMMARY OF THE INVENTION

The present invention comprises methods, apparati, and devices for the control of bleeding from an inner wall of a body passageway or cavity and for the plugging or closure of pathological cavities.

Briefly, the invention comprises an inflatable, expandable balloon, usually covered by a hemostatic shroud, which is inserted into a body cavity, such as a nasal passageway or intestinal diverticula. The shroud is composed of a fabric which exhibits hemostatic properties; that is, the shroud acts to facilitate or enhance blood clot formation. The balloon component of the present invention is expanded, or inflated, within the cavity in order to press the shroud against the site of bleeding, thereby allowing it to absorb blood and facilitate hemostasis. In specific embodiments, the shroud is composed of a woven or knitted fabric of a hemostatic fiber (such as carboxymethylcellulose) or a reinforced hemostatic fiber. Optionally, this shroud may include an "extension" or "tail" fiber, which upon balloon deflation and removal, facilitates the later removal of the shroud which has been intentionally left in vivo.

The device construction, particularly the balloon construction, may vary according to the particular body cavity. Although a range of different materials can be used for any of the embodiments, there are particular materials which work better than others, depending upon the particular application. For example, for a diverticula, the balloon is made of a highly elastic material such as silicone rubber. For a nasal application, however, the preferred construction is an inflatable, but non-stretchable, balloon made from a relatively inelastic material.

The invention also includes a method and device for controlling bleeding on an inner wall of a body cavity or passageway. The method comprises the step of inserting into a cavity a first inflatable balloon surrounded at least in part by a hemostatic shroud comprising a gel-forming absorbent composition. The expandable balloon is then expanded (inflated) which compresses the shroud against the inner surface of the cavity where bleeding is to be controlled. In nasal embodiments, during expansion of the expandable balloon and shroud, the pressure inside the expandable balloon can be monitored by touching a pressure-indicating pilot balloon which is in fluid communication with the first expandable balloon. The external tactile pressure sensing pilot balloon is located so that it does not enter the passageway. This allows a user to feel the pressure within the system as the first expandable balloon is inflated and permits monitoring of the first expandable balloon to avoid under-inflation or over-inflation. In the embodiment where the pilot cuff is used, a preferred pilot balloon is inflatable but non-stretchable, and has a fixed maximum volume.

Other aspects of the invention comprise methods for controlling bleeding in body passageways involving use of the devices described above.

A particular embodiment of the invention comprises a device for insertion of a shrouded balloon into a nasal passageway by a catheter configured such that the balloon encircles the catheter tube. The lumen of the catheter tube thereby serves as a passageway for breathing. The inflated balloon compresses the shroud against the bleeding nasal wall, thereby facilitating or enhancing hemostasis. The balloon is deflatable such that, upon balloon deflation, the shroud may be left in place on the cavity wall and may be removed at a later time, such as by an attached extension on the shroud.

In another embodiment, there is no central lumen. This gives the catheter a much smaller overall diameter. In patients with small nasal cavities, the lack of the breathing passageway is more than compensated for by the small profile which is far less traumatic and painful during insertion.

The shroud used in the present invention may comprise a woven or knitted fabric combining hemostatic (e.g., carboxymethylcellulose (CMC)) fibers with reinforcing fibers.

The invention also comprises methods and devices for the plugging of a cavity, such as a diverticulum, consisting of a catheter for the delivery and insertion into the cavity of a filling material, the filling material itself which is releasably connected to the catheter, and marker material for indicating the site of a cavity which has been plugged. Some examples of appropriate filling material include balloons which are designed to resist deflation, curable material, fibrous material, and resiliently deformable members. An anchor apparatus may be necessary in plugging a cavity if there is a chance that the filler material will be expelled by the peristaltic action of the digestive tract. These devices and methods may be used either to address a pathological situation or to act preemptively—i.e., to check the progression of diverticulosis to diverticulitis.

BRIEF DESCRIPTION OF DRAWINGS

For a better understanding of the present invention, reference may be made to the detailed description which follows, taken in conjunction with the drawings, in which:.

DETAILED DESCRIPTION OF THE INVENTION

The present invention comprises systems, devices, and methods for the control of bleeding in body cavities, such as nasal passageways, and for the plugging of pathological cavities, such as those associated with diverticular disease.

Generally, the terms "cavity" and "passageway" may include any bodily cavity, recess, passageway, etc., other than a blood vessel or other component of the vasculature system, and it encompasses those which are healthy and normal as well as those which are abnormal and/or pathological (meaning, diseased or unhealthy).

The term "hemostatic" agent (or material) refers to any agent or material that is capable of arresting, stemming, or preventing bleeding by means other than inducing tissue growth alone. In other words, something other than tissue growth is at least partially responsible for retarding or preventing bleeding. Preferably, the agent or material will be one that enhances blot clot formation. It will, of course, be appreciated that the agent or material may have the beneficial property of inducing tissue growth in addition to retarding or preventing bleeding. Examples of preferred hemostatic agents which enhance blood coagulation include carboxymethylcellulose (CMC), oxidized cellulose, calcium alginate, gelatine, or collagen. CMC can be purchased from Acordis Special Fibres, PO Box 111, 101 Lockhurst Land, Coventry, England, CV6 5RS. Oxidized cellulose such as Tabotamp™, which is sold by Johnson & Johnson, New Brunswick, N.J., U.S.A., is another example of a hemostatic agent. Combinations of different hemostatic agents or materials may be used within the scope of the invention.

Figure 4:
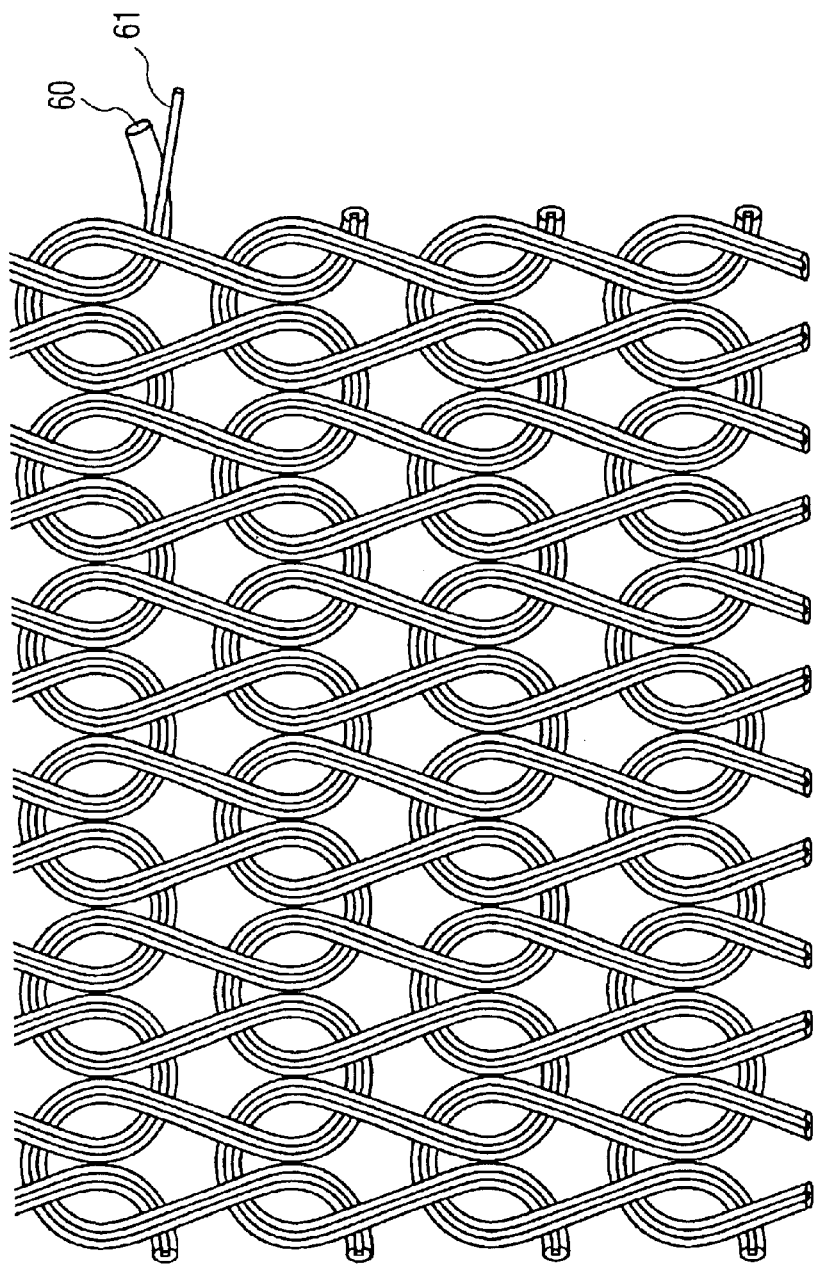
FIG. 4 is a schematic view of a knitted fabric structure useful in the present invention.

All embodiments of the present invention, other than those intended only to plug a pathological cavity, include an expansible hemostatic shroud, composed at least in part of a hemostatic material, which encircles an expansible device such as a balloon. The shroud may be in the form of an expandable tube or in the form of an expandable sheet. In the specific embodiments disclosed, the agent is a fibrous CMC, which is hemostatic and so will cause blood to clot while at the same time absorbing any exudate. A fabric of CMC fiber is preferred because, aside from its hemostatic properties, it swells and forms a gel, absorbing many times its own weight in fluid when it contacts water (or blood or exudate). Since the CMC material is so hygroscopic, it does not dry into the clotted blood, and therefore can be removed easily without tearing the clot and causing re-bleeding. Other hemostatic agents which may be used should have absorptive and hemostatic properties similar to those of CMC. In one embodiment, the hemostatic fibers are woven or knitted together with reinforcing fibers, such as continuous multifilament polyester or nylon. Such a knitted fabric as is illustrated in FIG. 4, is the sole invention of John Hudson, one of the inventors hereto, and will be more fully described and claimed in a separate application, filed on even date herewith and incorporated herein by reference. The use of reinforcing fibers provides increased strength to the shroud. This increased strength is important for successful removal of a blood-soaked fabric, where the CMC or gellable material has formed a gel and therefore lost much of its strength.

Examples of some other hemostatic materials include oxidized cellulose, which is conventionally used in knitted form as a hemostatic agent during surgery, and calcium alginate, which is a textile fiber derived from seaweed and is also commonly used as a wound dressing. Furthermore, there are other polysaccharides which are available with similar chemistry and properties to CMC. For purposes of the present invention, the essential properties of the hemostatic material are the ability to form a gel (or to swell) and to absorb large quantities of liquid. The material obviously must be non-toxic and biocompatible.

Preferably, the hemostatic shroud is provided in the form of a woven or knitted, especially a weft knitted, textile fabric in which is incorporated a hemostatic material, and which envelops the balloon. The woven or knitted textile material may be permanently or releasably fixed to the balloon.

Typically the balloon will be made of a relatively inelastic material in order to define a fixed volume. In such a case, the balloon is effectively a bag that can be filled or emptied with an inflation medium. A fixed volume, inflatable, non-expandable balloon does not require the inflating medium to first stretch the elastic material of the balloon (as would be the case where the balloon is made from an elastomeric material). All inflation medium pressure is used to fill the cavity. This is essential when the device is used with a pilot balloon to give a tactile feedback of the pressure inside the catheter balloon. With a non-elastic fixed volume balloon, the tactile feedback is truly representative of the pressure applied to the inner surface of the nasal cavity. For non-nasal applications such as diverticulae, an elastic material such as silicone rubber can be used for the balloon.

An inflatable, non-stretchable (inelastic) balloon would normally be used for a nasal application. It would typically be inflated with air and used in conjunction with a pressure monitoring device such as a pilot balloon.

An elastic balloon made from a material such as silicone rubber would normally be used for a diverticula application. It would be inflated with a liquid medium such as water or saline solution and the volume controlled by monitoring the volume of fluid inserted. Silicone rubber has the property of being permeable to air but not to liquid. A balloon of the type shown in FIG. 5 which has a built in non return valve may therefore be tested using air as an inflation medium which is then allowed to permeate out of the balloon. A vacuum chamber may be used to expedite this deflation.

Figure 1:
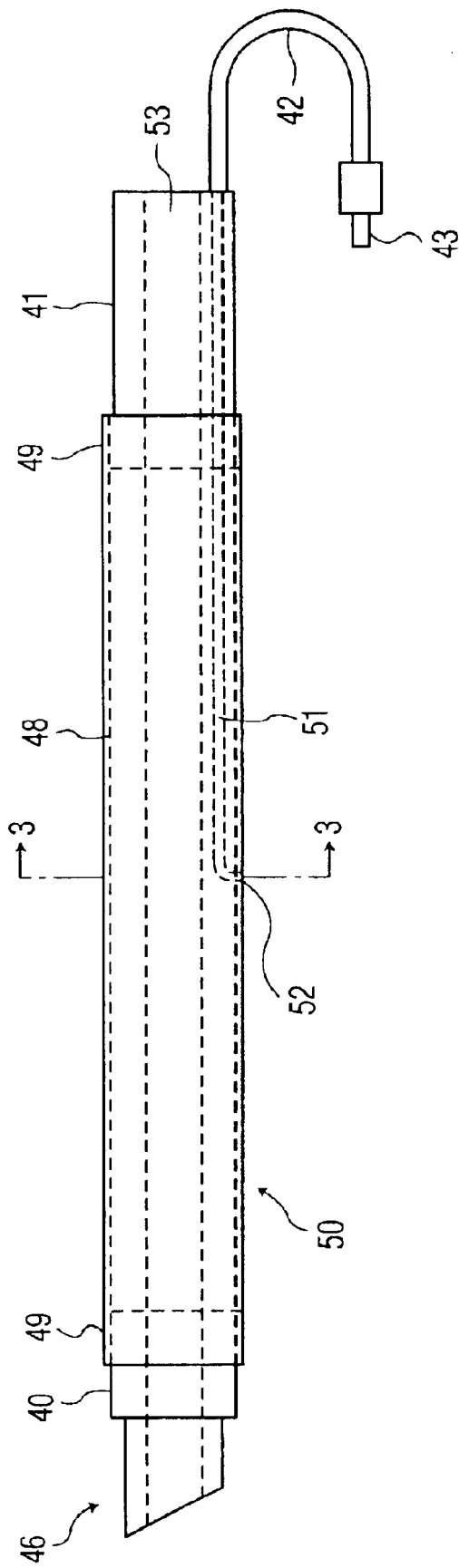
FIG. 1 is a side view of a component for a hemostatic component adapted for insertion in a nasal passageway.
Figure 2:
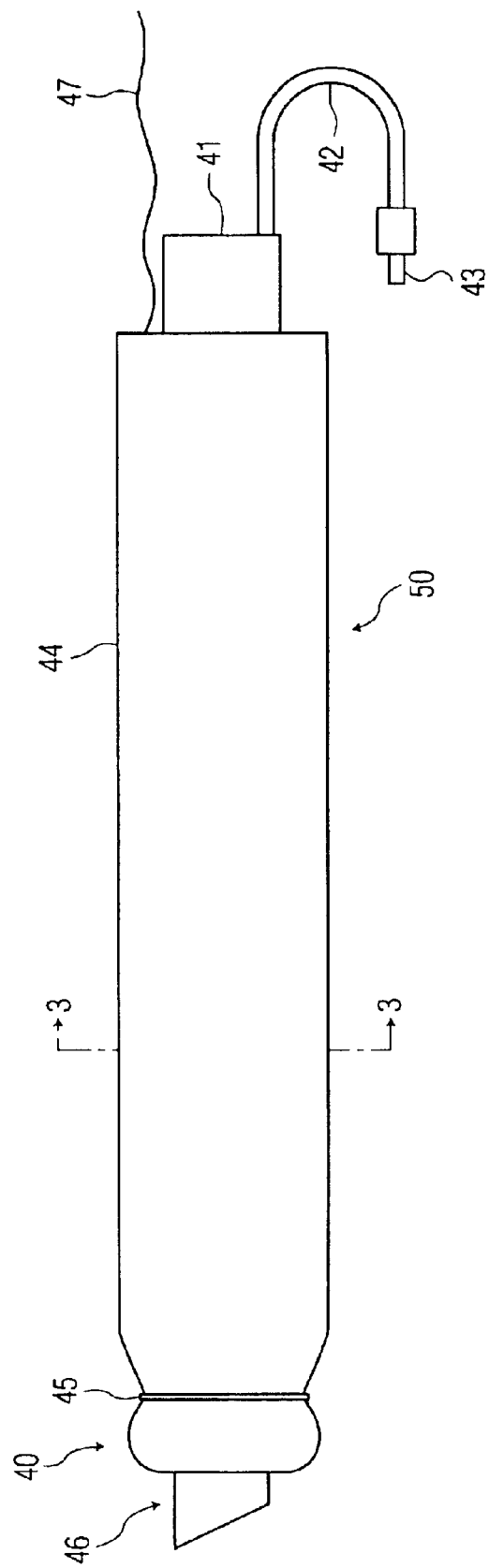
FIG. 2 is a side view of the component shown in FIG. 1 covered with a hemostatic shroud.
Figure 3:
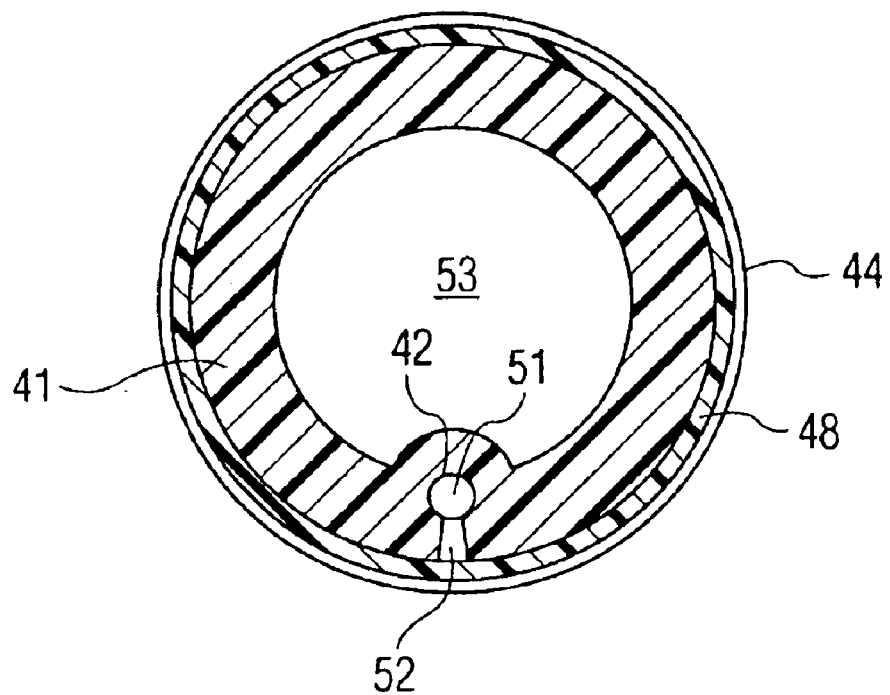
FIG. 3 is a cross-sectional view of the device shown in FIGS. 1 and 2.

A specific configuration of the present invention which is designed for insertion within a nasal passageway is depicted in FIGS. 1–3. As shown there, a balloon catheter 50 consists of a soft flexible elastomeric tube 41, with a long balloon 48 adhered to the outside wall of tube 41 along the end sections 49 of balloon 48. The wall of tube 41 includes an inflation lumen 51 (inflation passageway) which is in communication, through a thin tube 42, with a valve and luer 43 at one end and an inflation port 52 at the other end. The valve 43 is opened by the tip of a standard syringe by which the balloon 48 may be inflated or deflated at will. Tube 41 includes a central lumen 53 which serves as an air passage for breathing. In a specific exemplary embodiment, tube 41 has an approximate outside diameter of 10 mm, and an inside diameter of 4–5 mm. The active length is typically between 40 and 100 mm although shorter or longer lengths may be required for special applications. One end of catheter 46 may have a reduction in the outer diameter in order to provide a shoulder 40. This shoulder is used to locate and maintain the position of an outer hemostatic shroud, (seen in FIG. 2), during insertion of the device of FIG. 2 into a nasal passageway. In another method of construction the glued neck of the balloon supplies the shoulder and in yet another construction method no shoulder is used and the fabric is retained by a ring and glue or merely by glue alone. Catheter tube 41 typically is comprised of a silicone elastomer or some other material with similar properties such as, for example, PVC. In the embodiment of the present invention for use in a nasal passageway, the balloon should be of fixed volume with an expanded diameter of approximately 25 mm. Typically, the balloon is expanded by inflation with air.

FIG. 2. illustrates the balloon catheter component of FIG. 1 covered by a hemostatic shroud 44 which envelopes a portion of catheter tube 41. Hemostatic shroud 44 is a soft knitted or woven fabric tube made from a hemostatic material with a high absorption ability. Shroud 44 is draped around the balloon catheter 50 and is positioned by a sewn ring or ligature 45, which locates over shoulder 40 at the distal end 46 of the balloon catheter. The "ring over shoulder" mounting allows shroud 44 to be located precisely over balloon 48 when the device is inserted into the nasal cavity, but permits balloon 48 to be released from shroud 44 by simply withdrawing the catheter. Other methods of locating the shroud may also be used, such as a glued grommet, a welded ring, or by actually shaping the knitted shroud for retention on the balloon. The fabric shroud is highly elastic and deformable which allows it to stretch and/or deform as the balloon is inflated. An extension tail 47 to shroud 44 may be provided as a means to remove the hemostatic element separately after balloon 48 has been removed.

FIG. 3 shows a cross section, in the plane A–A', of nasal catheter 50 of FIGS. 1 and 2. As shown in FIG. 3, balloon 48, is covered by hemostatic shroud 44, encircling tube 41 and the non-adhered underside thereof is in communication with inflation port 52.

In service, balloon 48 is inflated by filling material, typically compressed air, from a syringe in communication with valve 43 and the inflation lumen 42 which terminates in port 52 at the inner surface of balloon 48 between the ends of the balloon which are adhered at tube surface areas 49.

FIG. 4 illustrates a schematic view of a preferred fabric for the hemostatic shroud. Specifically, spun CMC yarn 60 is knitted in parallel with a polyester reinforcing yarn 61, as more specifically described in the aforementioned U.S. Patent Application of Mr. Hudson to be filed separately. In this preferred embodiment, the knitted fabric tube is manufactured first by knitting a tube from Lyocell yarn in combination with the reinforcing filament. Lyocell is the generic name for solvent spun cellulose fiber. A brand thereof, "Tencel," (a registered trademark), is available from Accordis Fibres, Coventry UK. Lyocell is produced from the natural cellulose in wood pulp by dissolving the wood pulp in a solvent and then extruding the product through a die called a spinneret. The solvent is then evaporated therefrom, thereby leaving a fiber which is composed of pure cellulose. After knitting, the fabric tube is subjected to a sodium reactant, according to known techniques, which serves to convert the pure cellulose at least partially, into sodium carboxymethylcellulose. The chemical conversion process is similar to that used to make carboxymethylcellulose sodium USP, except that the raw cellulose is in fiber form rather than the more normal powder form. Other cellulosic raw materials can also be used such as cotton or viscose rayon.

The use of the hemostatic nasal device of FIGS. 1–3 involves inserting into the nasal cavity the shroud-covered balloon catheter 50 illustrated in FIG. 2. Balloon 48 is then inflated. Since the fabric shroud is elastic and deformable, it is able to expand and not limit the balloon in its ability to fill the cavity. The hemostatic fabric is pressed against the vessel wall and into contact with the blood. On contact with blood, the hemostatic fabric, typically CMC (or other similar material), adheres to the cavity wall and swells to form a gel. It absorbs blood and exudate while its hemostatic properties facilitate and enhance blood clot formation. The lumen of the large (catheter) tube provides for normal breathing, while the inflated balloon provides an anchor for the device. After hemostasis is achieved, the balloon 48 is deflated, and then the catheter is removed. In one embodiment the balloon and tube only are removed and the gelled fabric is left in situ.

Where the gelled fabric alone has been left in situ, then the fabric may be removed at any time by means of the withdrawal string or "tail" 47. Since the hygroscopic nature of the hemostatic fabric prevents the material from sticking to the clotted blood, removal is simple and with minimal chance of restarting the bleeding process.

In another embodiment of the present invention, a system and method are designed for insertion and retention of an expandable balloon into a body cavity. In this system, the balloon is expanded such that it resists deflation and such that it fills the interior of the cavity, thereby applying controlled pressure against the inner wall of the cavity at the site of bleeding.

In a particular exemplary embodiment, the balloon is associated with a hemostatic agent. Preferably, the hemostatic shroud is provided in the form of a net or knitted, especially a weft knitted, textile material that envelops the balloon. A more preferred embodiment includes a hemostatic shroud, releasable affixed on the outside of the balloon and composed of a fabric knitted with carboxymethylcellulose fibers and a reinforcing filament.

Conveniently, when used for a diverticula application, the balloon comprises an elastomeric material, such as silicone rubber. Preferably, the balloon is made from material that is impermeable to liquid but permeable to gas so that the balloon and material providing resistance to deflation can be tested before use by inflating the balloon with air. If there are no leaks, the balloon can be deflated by placing it is a vacuum chamber for 2–3 hours which causes the air to permeate through the balloon wall.

In one embodiment, the balloon is an expandable balloon having an inflation port including a non-return valve arrangement. Such an arrangement allows the balloon to be inflated irreversibly—if desired—by entry of a filler material, such as water or air, through the inflation port. The luer type valve is designed to be used to prevent the balloon from deflating.

In another embodiment, the non-return valve comprises a tube sealed at one end having an outlet in the side wall, the outlet being releasably sealed with a valve cover. The valve cover being formed from part of the balloon, more specifically from part of the neck of the balloon.

In an alternative embodiment, the outer surface of the balloon is coated with an agent which facilitates blood coagulation. Examples of coating material include gelatin and collagen, but the invention is not limited to these.

It should be appreciated that if the hemostatic agent is relatively fast-acting, the balloon catheter can be configured in such a way that it need not be provided with the capability of resisting deflation. The balloon can simply be pushed inside a cavity until the bleeding has been prevented, controlled, or stopped, and then removed.

Another aspect of the invention provides a system and method for plugging a cavity—for example, a pathological cavity associated with incipient or actual diverticulosis. Such a method comprises the insertion of an expandable balloon into the cavity and expansion of the balloon such that it resists deflation and is retained within the cavity.

The term "filling material" is intended to include any material and/or apparatus which can be inserted into, and substantially fill, a cavity, preferably a pathological cavity such as a diverticulum, to inhibit and preferably prevent, amongst other things, bleeding and the ingress of deleterious substances such as fecal matter (in the specific case of diverticula).

In one particularly exemplary embodiment, the "filling material" comprises an inflatable balloon. The balloon is inflated within the body cavity.

In another embodiment, the "filling material" comprises a curable material which can be used in non-solid form (e.g., as a liquid, paste, or gel form) to fill a cavity such as a diverticulum, and then cured into a hardened state. The curable material should be biocompatible and quick-setting so that the procedure can be conducted rapidly. Examples of suitable curable materials include silicone elastomers, polyurethane foam or elastomer, or epoxy resins. Setting or curing of the material can be effected by solvent evaporation, ultra violet light or visible irradiation, or by heating. The curable material may be provided in two or more parts for mixing outside or within the cavity.

The term "bio-compatible" is intended to mean being harmonious to life and not having toxic or injurious effects on biological function. For this particular aspect of the invention, this term is also intended to embrace material which has a slightly irritant or thrombogenic effect in a host organism. Such an effect may be useful to promote tissue growth over a plugged diverticulum.

In a further embodiment, an anchoring apparatus is inserted into the cavity along with the curable material in order to retain the cured material within so that it will not be expelled before it is cured. In the specific case where the cavity is a diverticulum, the anchoring apparatus would help prevent the expulsion of the material as a result of the peristaltic action of the colon.

The term "anchor apparatus" is intended to embrace any physical means by which the balloon or other filling material can be retained within a cavity. For example, an apparatus may include one or more fingers, barbs, or springs which can attach or lodge onto the interior wall of the cavity and prevent the material from being expelled. In one embodiment, penetration of the interior wall of a cavity by an anchor apparatus is limited by one or more abutment means. In one particular embodiment, the anchor is constructed from a shape memory alloy, a superelastic material or an elastic material, more preferably from nitinol, tempered steel, or a molded plastic such as a thermosetting or thermoplastic plastic.

The term "shape memory alloy" is meant to indicate an alloy which can be preformed into a first preferred shape while hot, then cooled, and folded into a second shape, the second shape remaining fixed until the alloy is heated whereupon it returns to its first preferred shape.

Use of such alloys advantageously permits the anchor apparatus to be folded from a first preferred shape into a second shape which is small enough to fit into the end of a catheter. After insertion into a cavity such as a diverticulum, the anchor returns to its preferred shape due to the heat of the patient's body.

By the term "superelastic material," we mean a material which has elastic properties such that a large change in strain is accompanied by a relatively small change in stress. That is, a material which has a modulus of elasticity (Young's modulus), close to zero.

In a further embodiment of the present invention, the "filling material" comprises a fibrous material such as a textile thread or fiber. Preferably the threads or fibers are coated with an adhesive material. The adhesive material can be applied before, after, or at the same time the fibrous material is inserted into a cavity such as a diverticulum. Examples of suitable adhesives include Fibrin glues; non-toxic thermosetting elastomeric adhesives such as moisture and UV light curing types and cyanoacrylates. Some examples may be found in the range of medically approved products distributed by Loctite UK Ltd.

In a particular embodiment, an anchor apparatus is provided to retain the fibrous material within the cavity.

In yet another embodiment of the invention, the "filling material" comprises a resiliently deformable member, such as an elastomeric member. In use, the elastomeric member is compressed, inserted into a cavity and released so that it expands to fill said cavity.

By "resiliently deformable member" we include the meaning of a member which can be deformed from a retaining shape in which it can be retained inside a cavity such as a diverticulum, to a smaller shape in which it can be inserted inside said cavity. The term "resiliently" is used to denote that the member can return to its retaining shape under suitable conditions.

Again, in a particular embodiment, the deformable member is provided with an anchor apparatus constructed and arranged to retain the member within the cavity.

Cavities, such as diverticula, which have been treated using materials and methods according to this aspect of the invention may be marked by a "marker material" to distinguish them from untreated cavities. The "marker material" may be visible to the naked human eye without extracorporeal detection or visualization means, even though in practice the person performing the treatment may use such visualization means (e.g., an endoscope). Hence, the term "visible to the naked human eye" is not intended to embrace, for example, a radiopaque agent which is invisible to the human eye without the aid of radioactive detection means such as a gamma camera. Suitable marking can be achieved in a variety of ways. For example, a marker "flag" can be provided in the form of an attachment to the balloon which protrudes from the neck of a cavity which has been filled. Also, a marker "flag" can be provided in the form of an attachment to the filling material and/or anchor apparatus. Such a flag may be composed of a biodegradable material such as sodium alginate.

Alternatively or additionally, a dye can be used as a marker. The dye can be applied as a spray, or as an injection (i.e., a tattoo). Preferred dyes include 5% methylene blue, Lugol's solution, toluidene blue, 1:4 solution of washable blue ink, and 0.1% indigo carmine. A suitable tattoo medium could be an aliquot of sterile Indian ink, diluted 1:100. The use of dyes is within the knowledge of a skilled person.

In a preferred embodiment of the invention, a catheter is used to insert the filling material into a cavity such as a diverticulum. An example of a suitable catheter is one that has a recess for receiving the filling material, a release mechanism for releasing the material from the catheter, and, optionally, the capability for injecting the filler material into the cavity. Additionally, the catheter comprises an inner and an outer tube, the inner tube slidably engaging the outer tube and having the capability for receiving the filling material at one end and for injecting said material at a second end. The outer tube has an end portion outwardly extending from one end of the inner tube defining the recess for receiving the filling material with the second end of the outer tube being joined to the inner tube by a seal. The release mechanism, in use, reciprocates the outer tube relative to the inner tube. In this particular arrangement, the outer tube sits over the mouth of a cavity such as a diverticulum and acts as a restraining brace while the filling material is inserted into the diverticulum. Once the cavity is filled, the injection means is disassociated from the filler material. This prevents application of any undue force to the inside of the cavity and further accelerates the encapsulation of the filling material by body tissue.

In a particular embodiment, the seal joining the outer tube to the inner tube has an inlet port for receiving a biocompatible fluid. This enables the Endoscopist to flush any body tissue from the recess restraining the filling material or to wash the inside of a cavity prior to the insertion of the material. Alternatively, the Endoscopist may pass a dye through the inlet port and spray mark the cavity which has been filled. This permits the Endoscopist to quickly identify which cavity or cavities have been plugged, thus increasing the efficiency of the overall process.

Advantageously, the outer surface of the balloon is textured or roughened to increase its surface area and, in use, promote tissue growth to encapsulate the balloon and thereby close a cavity, especially a pathological cavity such as a diverticulum. To further promote the growth of tissue, a tissue growth promoting agent can be provided. For example, the outer surface of the balloon may be coated with a growth-promoting agent in the form of a bio-absorbable polymer such as polyglycolic acid. Other growth-promoting agents include polysaccharides, polyactic acid (PLA), polyactide, cellulose esters, polycaprolactone, polyethylene glycol, polyphosphate ester, collagen, polydioxanone (PDS), trimethylene carbonate (TMC), hyaluronic acid (HLA), and other glycosaminoglycans which are within the knowledge of a skilled person.

Inflatable Balloon

Figure 5:
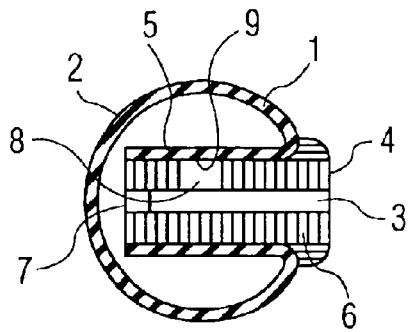
FIG. 5 is a longitudinal cross-section of a balloon for another embodiment of the present invention, namely a system and method for the insertion and filling of a body cavity, such as a diverticulum;.
Figure 5A:
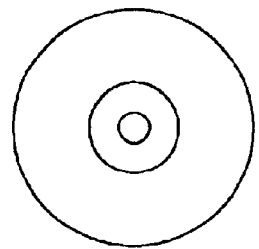
FIG. 5a is an end view of the uninflated balloon of FIG. 5.

FIG. 5 shows a preferred embodiment of the invention comprising a balloon 1 having a coating of a hemostatic agent 2, and inflation port 3, and a non-return valve 4. The balloon is preferably made from an elastomeric material, such as a thin silicone polymer, by methods known to those skilled in the art, such as by dip molding.

In a more preferred embodiment, the agent is provided as a shroud, as a knitted fabric which is draped over the balloon.

The inflation port 3 and/or non-return valve 4 is preferably made from a silicone polymer and is affixed to the balloon by gluing with a silicone adhesive or other affixing methods which are within the knowledge of a skilled person in the art. The neck 5 of balloon 1 is turned inside out and placed over non-return valve 4. The balloon is then glued to the front edge of the non-return valve only so that the neck 5 of the balloon grips the outer wall of non-return valve 4.

Figure 6:
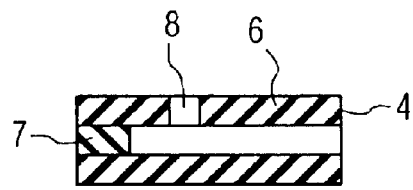
FIG. 6 is a partial cross-sectional view of a non-return valve for a device adapted for insertion into and filling of a body cavity.
Figure 6A:
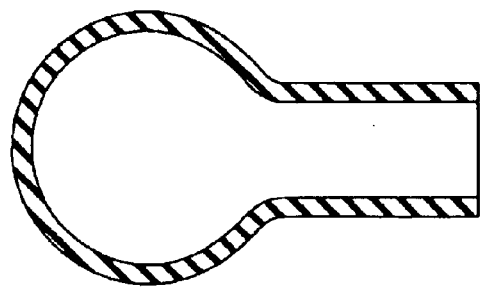
FIG. 6a is a cross-section through the balloon in FIG. 5 prior to stem inversion.

The non-return valve 4, as shown in FIGS. 5 and 6, is made from an elastomeric material, such as a thin silicone elastomer by methods known to those in the art, such as injection molding.

Preferably, non-return valve 4 is a tube 6 having a seal 7 which seals one end and an outlet 8 in its side wall. Outlet 8 is covered by the neck 5 of the balloon 1 which grips the outer wall of valve 4 and functions as a valve cover.

In an embodiment comprising a method of plugging a cavity, the outer surface of the balloon is textured or roughened to increase its effective surface area, thereby promoting tissue growth and encouraging complete encapsulation of the balloon in use. Preferably, the balloon is also coated with an abrasive material. Additionally, or alternatively, the balloon may be coated with an agent to promote further tissue growth and encourage rapid encapsulation. The growth promoting agent may be one or more of a number of bio-absorbable polymers, especially a polyglycolic acid (PGA), or one or more of polyactic acid (PLA), polyactide, cellulose ester, polycaprolactone, polyethylene glycol, polyphosphate ester, collagen, polydioxanone (PDS), trimethylene carbonate (TMC), hyaluronic acid (HLA), and other glycosaminoglycans.

Figure 12:
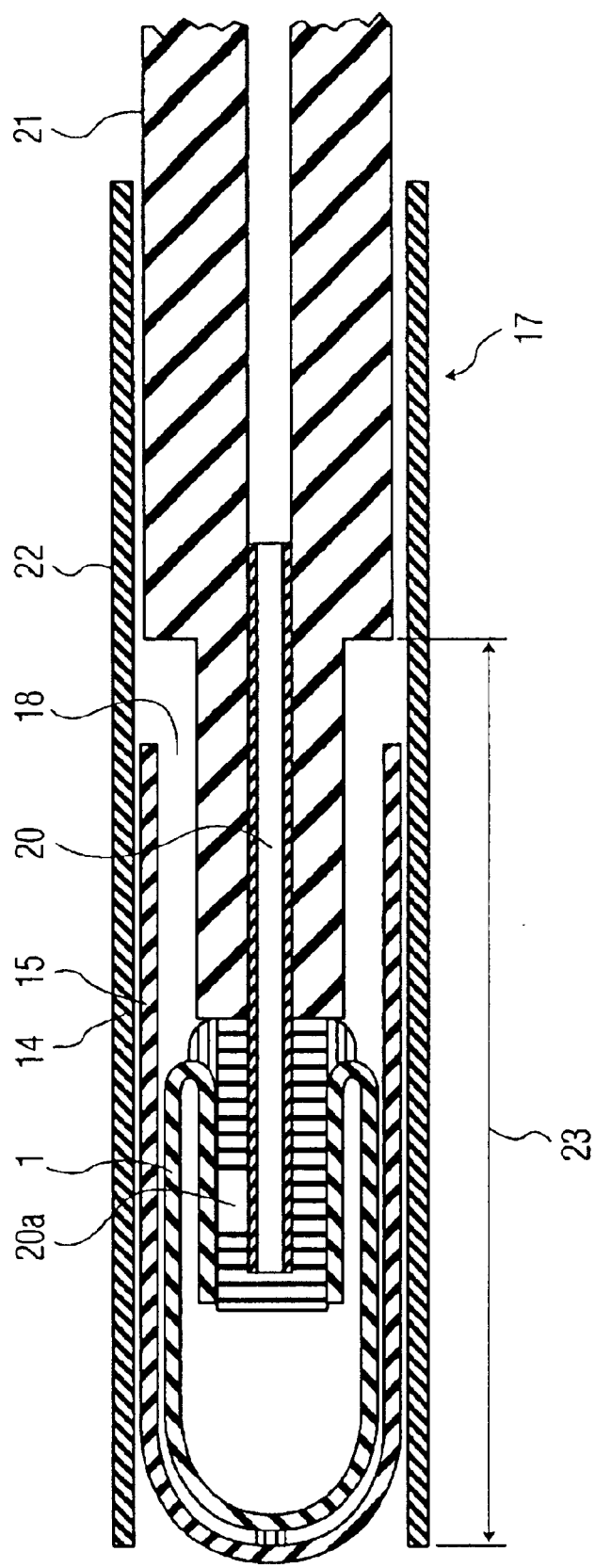
FIG. 12 is a partial cross-sectional view of the balloon of FIG. 5 mounted at the distal end of a catheter, which is an embodiment of a method and device for delivery.
Figure 13:
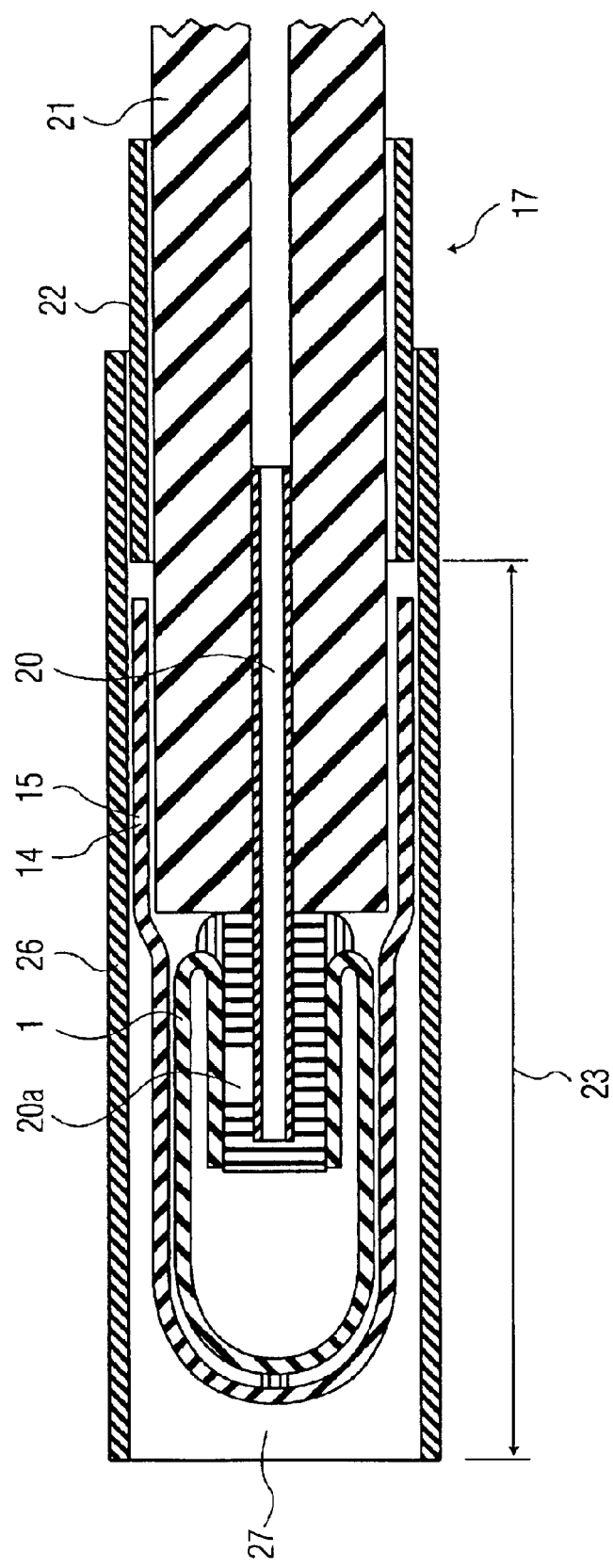
FIG. 13 is a schematic view of an embodiment of a system and method for the insertion and filling of a balloon into a body cavity. It is a partial cross-sectional view of a balloon mounted at the distal end of a catheter having a shroud.

Preferably the balloon is inserted in the end of a catheter, as shown in FIGS. 12 and 13. This allows the balloon to be delivered into a cavity such as a diverticulum via the working channel of a conventional endoscope.

Alternative Embodiment with Optional Anchor Means

Figure 7:
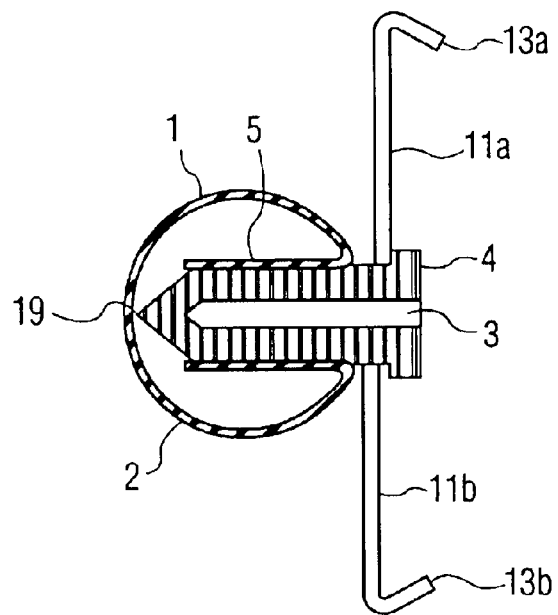
FIG. 7 is a longitudinal cross-sectional view of an embodiment of a system configured for the insertion and filling of a body cavity comprising a balloon having an anchor apparatus.

FIG. 7 illustrates one embodiment of the invention, in the form of a balloon 1 having an alternative inflation port 3 and/or non-return valve 4 in an inflated condition having an anchor apparatus 10 in a retaining position.

Figure 11:
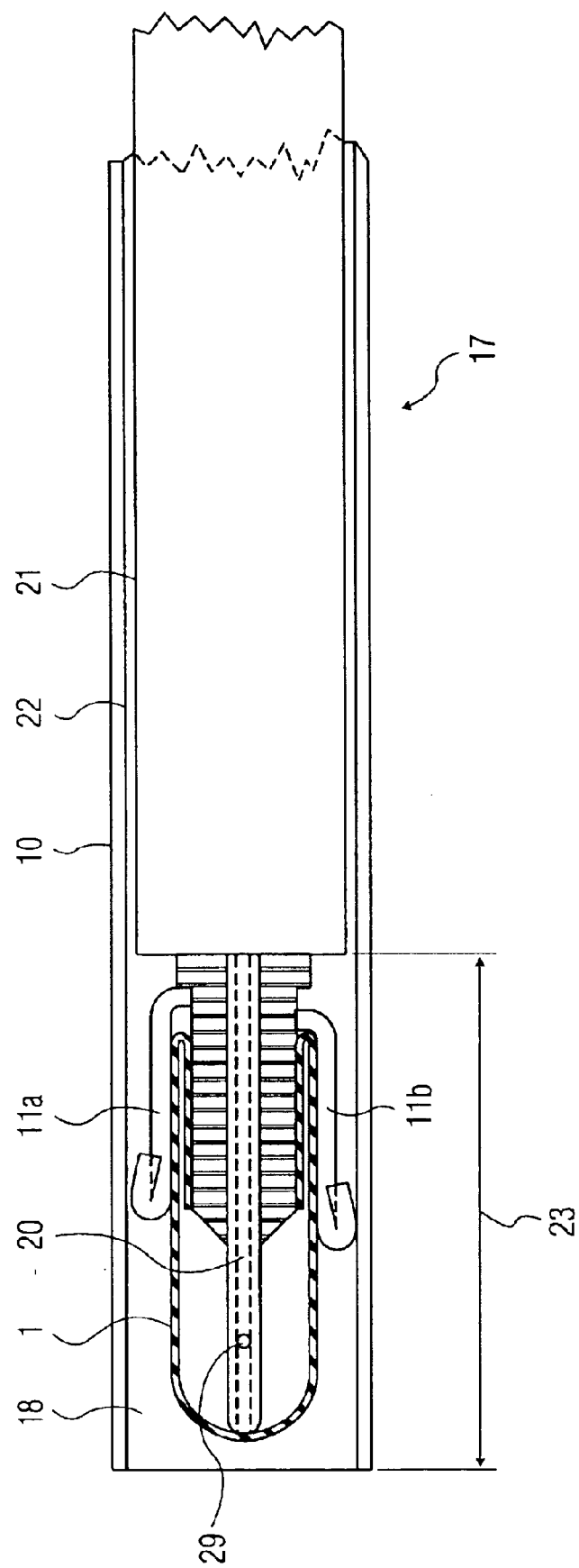
FIG. 11 is a partial cross-sectional view of the balloon of FIG. 7 mounted at the distal end of a catheter, which is an embodiment of a method and device for delivery.

In this embodiment, the biocompatible fluid is introduced into balloon 1 causing it to pass through an opening 19. The opening is created when opposite portions of non-return valve 4 are forced apart. One such method is illustrated in FIG. 11. FIG. 11 shows an injection device inserted through opening 19. An injection device 20 may be a hypodermic needle. Because the non-return valve 4 is made from a flexible material, the opening 19 seals against itself when the injection device 20 is withdrawn.

Figure 8:
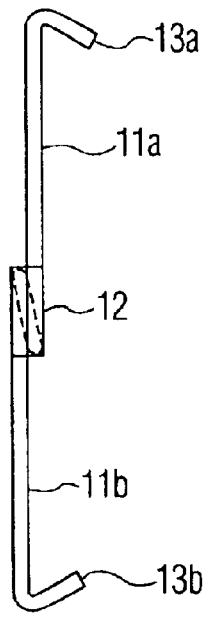
FIG. 8 is a side view of the anchor apparatus of FIG. 10.
Figure 9:
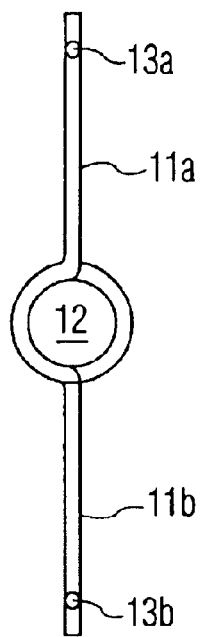
FIG. 9 is a front view of the anchor of FIG. 10.

As shown in FIGS. 7 to 10, anchor 10 has two arms 11a and 11b which, in the first retaining position shown, extend radially outwards from balloon 1. As shown in FIGS. 8 and 9, the two arms 11a and 11b are of equal length and extend radially from diametrically opposed points of a central hub 12. The two arms 11a and 11b have barbs 13a and 13b at the ends furthermost from the central hub.

Anchor 10 may be connected to the inflation port 3, or more alternatively, as shown in FIG. 7, connected to the combined inflation port 3 and non-return valve 4. Anchor 10 can, of course, be connected to the balloon by any known technique.

In one embodiment, anchor 10 is constructed from the shape memory alloy nitinol which is available from Euroflex Schussler GmbH, KaiserFriedrich, Str 7, D-75172, Pforzhehn, Germany. The anchor can be folded from a first retaining position (shown in FIG. 10 for example) into a second deformed condition in which it is small enough to allow the balloon to be inserted into a suitable delivery device, as shown in FIG. 11.

Figure 15B:
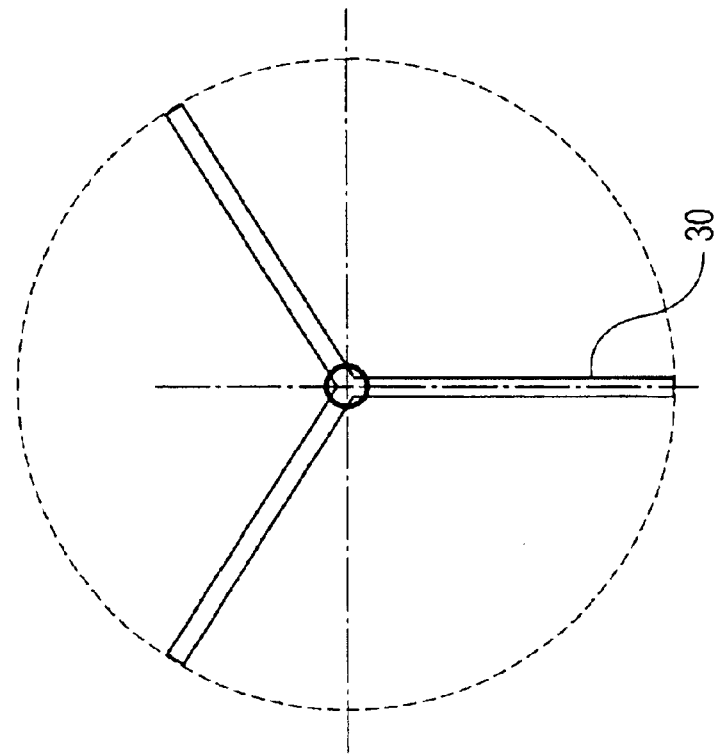
FIGS. 15a and 15b are side and end views, respectively, of an embodiment of an anchor apparatus.
Figure 15A:
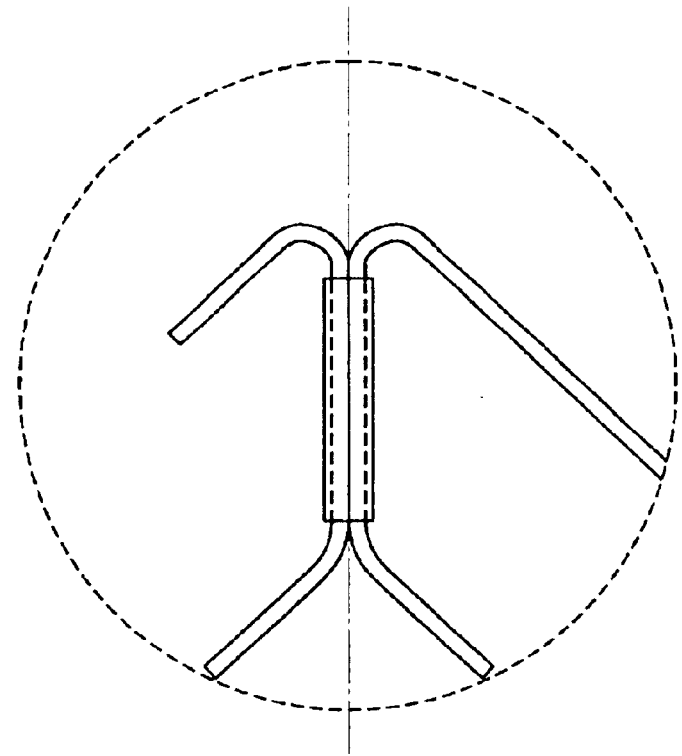

An alternative anchor arrangement 30 is shown in FIGS. 15a and 15b. The anchor is made from nitinol wire and or nitinol tubing.

Figure 16B:
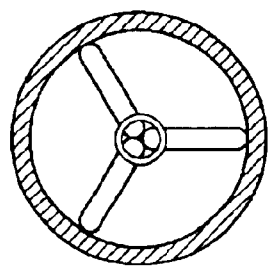
FIGS. 16a and 16b are partial cross-sectional side and end views, respectively, of the anchors of FIGS. 15a and 15b which are mounted at the distal end of a catheter.
Figure 16A:
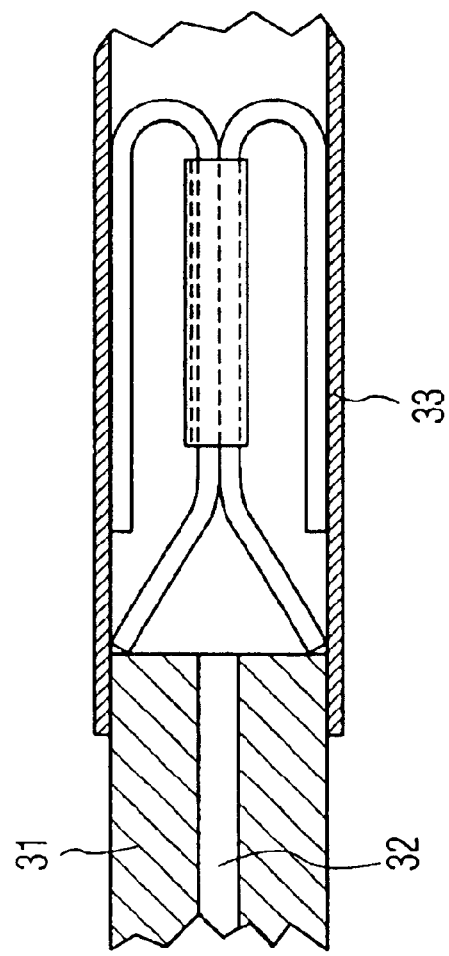
Figure 17A:
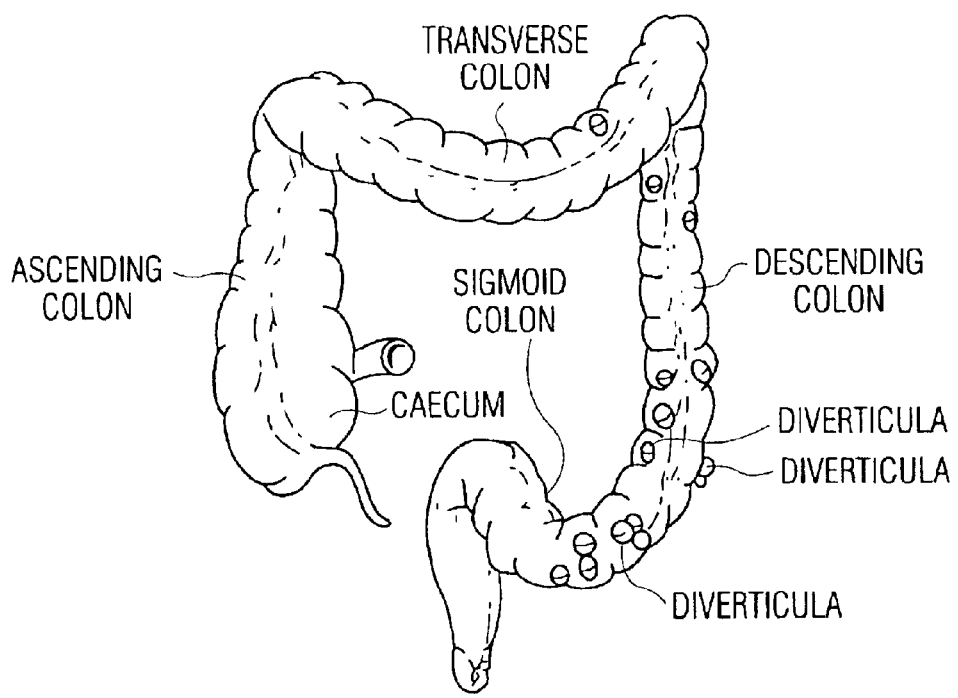
FIG. 17a illustrates diverticula of the colon.
Figure 17B:
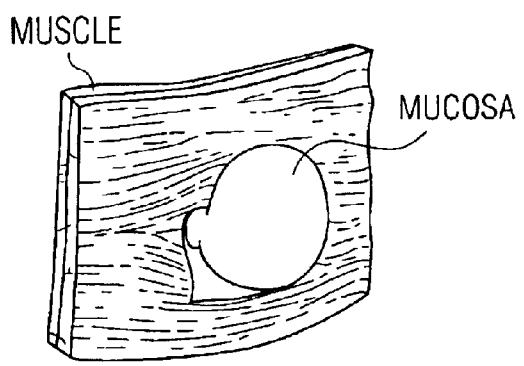
FIG. 17b shows a diverticulum formed by herniation of the intestinal mucosa through the weakened muscular wall at the site of arterial penetration on the mesenteric border of the colon.
Figure 17C:
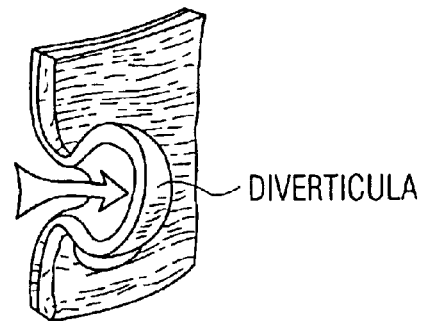
FIG. 17c illustrates how fecal matter can accumulate within the diverticulum.

FIGS. 16a and 16b show the anchor 30 mounted inside the distal end of a catheter having an anchor ejector tube and a central lumen for spraying or injecting a marker dye.

An anchor constructed of nitinol can easily be formed on a jig from a piece of nitinol wire, fixed by a simple heat treatment in a muffle furnace for example, so that the nitinol is set into its first retaining position.

Alternative methods of making the anchor include standard techniques known to those skilled in the art, for example, by stamping sheet material, from a tube or a combination of these methods.

Marker Material

According to one embodiment of the invention, a flag (not shown) is attached to the anchor and protrudes from the neck of a cavity (such as a diverticulum) after the anchor has been inserted. The flag is constructed from either a water-soluble or biodegradable polymer so that it is quickly absorbed after the procedure, such as calcium alginate.

Hemostatic Agent

According to the present invention, balloon 1 is associated with an agent that prevents or retards bleeding 2, especially by facilitating clot formation (hemostatic agent). The presence of such hemostatic agent serves to shorten the time needed to stop bleeding—arterial bleeding, especially—compared to the time needed with a balloon alone.

According to one exemplary embodiment, agent 2 is a fibrous version of carboxymethylcellulose, oxidized cellulose, calcium alginate, gelatine or collagen, advantageously in the form of a net 14 or knitted textile material 15 that envelopes balloon 1. Net 14 or knitted textile material 15 is glued to the distal tip of balloon 1 with a small amount of silicone adhesive, as shown in FIG. 12.

Alternatively, agent 2 is provided in the form of a flexible film (not shown) that coats the outer surface of the balloon. Balloon 1 is coated with the flexible film by conventional methods.

In an arrangement configured to plug a body cavity, the net 14, knitted textile material 15, or the flexible film is textured or roughened to increase its effective surface area, thereby promoting tissue growth and encouraging complete encapsulation of the balloon in use.

Delivery Device

As shown in FIGS. 11, 12, and 13, a preferred delivery device for inserting the balloon into a cavity such as a diverticulum is a catheter 17. Catheter 17 is also the preferred means for inflating the balloon by delivering and filling with a filling material. In one particular embodiment, catheter 17 has a recess 18 for receiving the balloon, a release mechanism (not shown) for releasing balloon 1 from the catheter and an injection means for delivering and filling said balloon with a filling material, thereby causing its expansion. As shown in FIGS. 11 through 13, the catheter comprises two coaxial tubes: an inner tube 21 that is slideably engaged with an outer tube 22.

An example of a means of injection 20 is a hypodermic needle with a hole 29 as shown in FIG. 11. The hole must be of a size sufficient to allow the biocompatible fluid to enter the balloon 1 in a desired time. One skilled in the art would not have a difficult time selecting a hole size sufficient to achieve this purpose.

Alternatively, balloon 1 may be inflated by passing a biocompatible fluid through an opening 20a as shown in FIG. 12. The balloon wall which covers opening 20a is displaced under the pressure of the biocompatible fluid as it flows into balloon 1.

Figure 14:
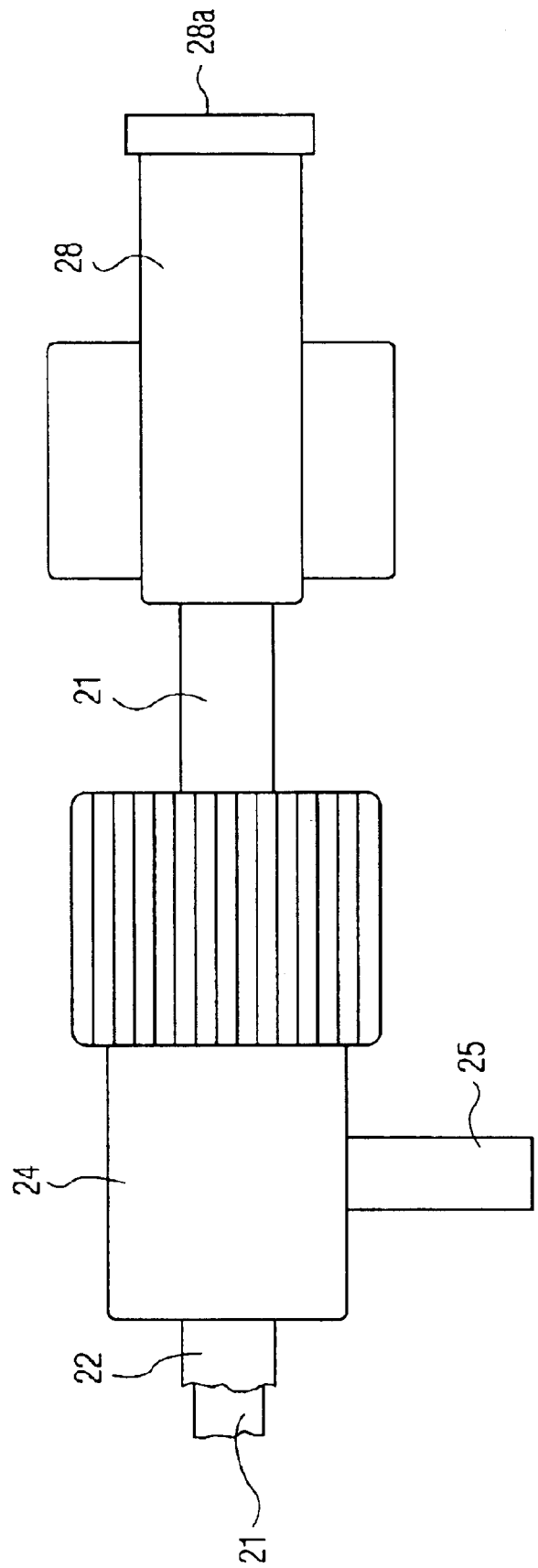
FIG. 14 is a partial side view of a proximal end of a catheter, which is an embodiment of a method and device for the delivery of a filling material to a body cavity.

As shown in FIGS. 11 and 12, the distal end of outer tube 22 has an end portion 23 which extends outwardly from the distal end of inner tube 21, thereby defining the recess 18 to receive and constrain balloon 1 prior to insertion into a cavity such as a diverticulum. As shown in FIG. 14, the proximal end of outer tube 22 is connected to inner tube 21 by a seal 24 having an inlet port 25 to receive a biocompatible fluid such as water into the space between the inner and outer tubes. In one embodiment, seal 24 is a "Toughy-Borst" connector which is available from Qosina Company of 150-Q Executive Drive, Edgewood, N.Y., 11217 U.S.A. The bio-compatible fluid can be used to flush recess 18 and thereby remove any body tissue, or for washing the inside of a cavity (in the specific case of a diverticulum, fluid can be used to rinse out any accumulated material such as fecal material), prior to the insertion of balloon 1. Alternatively, or additionally, the fluid may be a dye for marking a cavity that has received a balloon.

Alternatively, or additionally, as shown in FIG. 13, the distal end of outer tube 22 has a sheath 26 slideably attached thereto. Sheath 26 permits a larger diameter balloon or a standard size balloon having a thicker hemostatic net 14 or a thicker hemostatic knitted material 15 to be carried by catheter 17 which, in use, allows cavities of varying sizes to be plugged.

The proximal end of the inner tube 21, as shown in FIG. 14, terminates with a standard luer pressure tight connector 28 having a stopcock 28a for receiving a pressure controlled inflation device (not shown) having a monitor for both volume and pressure. Such a pressure tight connector is also available from Qosina Company.

In a specific embodiment, the pressure controlled inflation device is a normal 30 ml syringe used in standard angioplastic procedures with balloon catheters. The syringe has an accurate graduation for measuring the volume of fluid injected into the balloon. It is also fitted with a pressure gauge that monitors pressure in the region of 0 to 100 kPa (0 to 15 psi). In use, pressure and volume measurements enable the balloon to be fully inflated inside the cavity whilst reducing the risk of bursting the cavity, which could lead to serious breaches in the corresponding bodily system (in the case of a diverticulum which ruptures, it could lead to a perforation in the peritoneum).

Preferably, the length of the continuous double tube is greater than 2.25 meters. Preferably, the outer tube has an outside diameter of between 7–12 French (2.5–4.0 mm), so that it is able to fit inside the working channel of a conventional endoscope.

The distal end of the inner tube 21 terminates in an injection means 20 for delivering to and filling the balloon with a filling material which is generally a bio-compatible fluid such as water.

Injection means 20 may be permanently sealed to the distal end of inner tube 21 using standard methods, or be removeably/releasably sealed to the distal end of inner tube 21 using standard methods, for example a screw thread type connection. According to one embodiment, injection means 20 is a nozzle, a tubular member or an injection needle. Additionally or alternatively, the outer diameter of injection means 20 is slightly larger than the relaxed inner diameter of inflation port 3 and/or non-return valve 4 of balloon 1. This results in a frictional force between injection means 20 and inflation port 3/non-return valve 4 which, in use, retains balloon 1 on the injection means.

At the proximal end of the continuous double tube catheter is the release mechanism (not shown), that moves the inner tube within the outer tube by an amount not less than the length of the inflation device that is mounted at the distal end of inner tube 21 and constrained by outer tube 22.

Pilot Balloon Tactile Pressure Indicator

In yet another embodiment, the device of this invention may include a tactile pressure-indicating pilot balloon in fluid communication with the balloon by which pressure is exerted on the hemostatic shroud. In such an embodiment, both the shroud compressing balloon and the pilot balloon are expandable. Preferably, both balloons are inflatable but made of a non-stretchable material. In this embodiment, the "balloons" are really more like bags or plastic sacks which receive an inflation medium such as air. Once the balloon is fully inflated, its volume no longer changes because the material of which it is made does not stretch. In use the balloon will never be inflated to its maximum volume because the cavity into which the balloon is inflated will always be smaller than the theoretical maximum volume of the balloon. This is because the maximum volume and dimensions of the balloon are chosen to be larger than the cavity in order that the balloon always has the capacity to fill the cavity. In this way, the hemostatic shroud, which surrounds the balloon, is pressed against the complete inner surface of the cavity.

Figure 19:
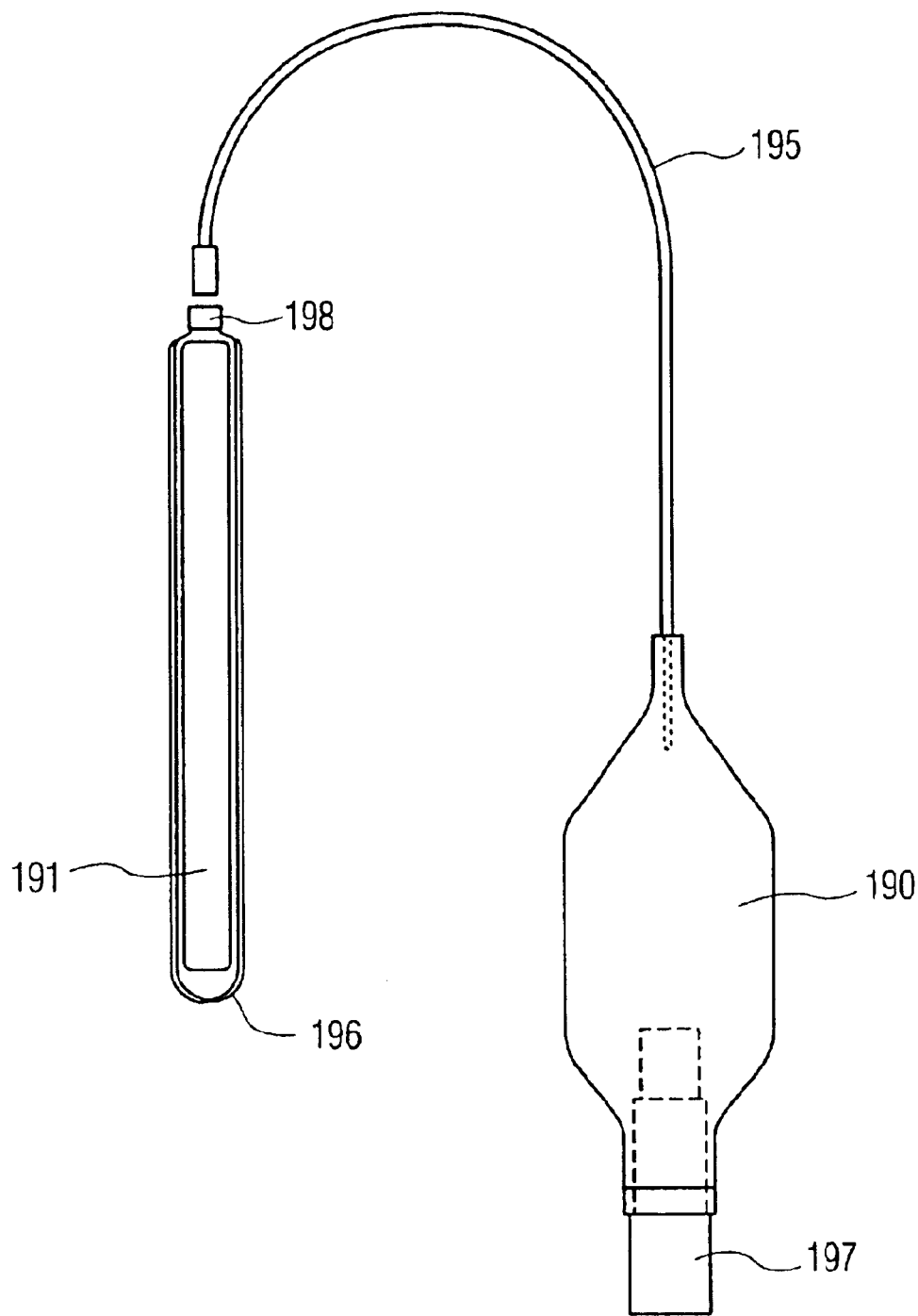
FIG. 19 illustrates still yet another embodiment of the invention which uses a pressure-indicating pilot balloon.

Such a pilot balloon may be disposed at the end of the inflation tube opposite the inflatable balloon of a nasal device as shown in FIG. 19. In this embodiment, pilot balloon 190 is connected to first inflatable balloon 191 via inflation tube 195. Thus, the external tactile pressure sensing pilot balloon 190 does not enter the passageway but allows the user to feel the pressure (usually by grasping the pilot between thumb and finger) within the system as the first inflatable balloon 191 is inflated. The pilot balloon 190 inflates along with inflatable balloon 190 during placement of hemostatic fabric 196 because the two balloons are in fluid communication with each other. Thus, during placement, the doctor is able to touch the pilot balloon and feel the pressure increase as the system inflates. As discussed above, this may be particularly important in nasal passageway applications because too little inflation pressure may result in a lack of blood flow stopage, and too great an inflation pressure may damage the passageway. Thus, through a careful tactile determination of system pressure during inflation and placement of the hemostatic fabric, proper and effective use of the device is insured.

In order for the tactile pressure sensing pilot balloon to give a more accurate indication of the pressure inside the nasal cavity, it is preferred that the first inflatable balloon (catheter balloon) be non-stretchable. In accordance with this aspect of the invention, the balloon is made of a relatively inelastic material in order to have the ability of completely filling a cavity without any energy being used to stretch the wall of the balloon. In such a case, the balloon is effectively a bag that can be filled or emptied with an inflation medium. The inflatable, non-stretchable balloon does not require the inflating medium to first stretch the elastic material of the balloon (as would be the case where the balloon is made from an elastomeric material). This is preferred when the device is used with a pilot balloon to give a tactile feedback of the pressure inside the catheter balloon. With a non-stretchable balloon, the tactile feedback is representative of the pressure applied to the inner surface of the nasal cavity.

FIG. 19 also illustrates hemostatic fabric 196 disposed on first inflatable balloon 191. As discussed above, various means for introducing air or other suitable pressurizing fluid into the system can be used. FIG. 19 shows a Luer slip valve 197 attached to one end of a pilot balloon 190 the opposite end of which is connected via inflation tube 195. Such slip valves are known to those skilled in the art to provide the introduction of an inflating medium, typically air, into the system. Also shown in FIG. 19 is fabric clamp ring 198 used to hold the hemostatic fabric 196 to the inflation tube and/or base of inflatable balloon 191. In this embodiment, inflation tube 195 ends where inflatable balloon 191 and inflation tube 195 connect at clamp ring 198. In the alternative embodiment shown in FIG. 20, an inflation tube 200 actually extends into inflatable balloon 191.

Figure 20:
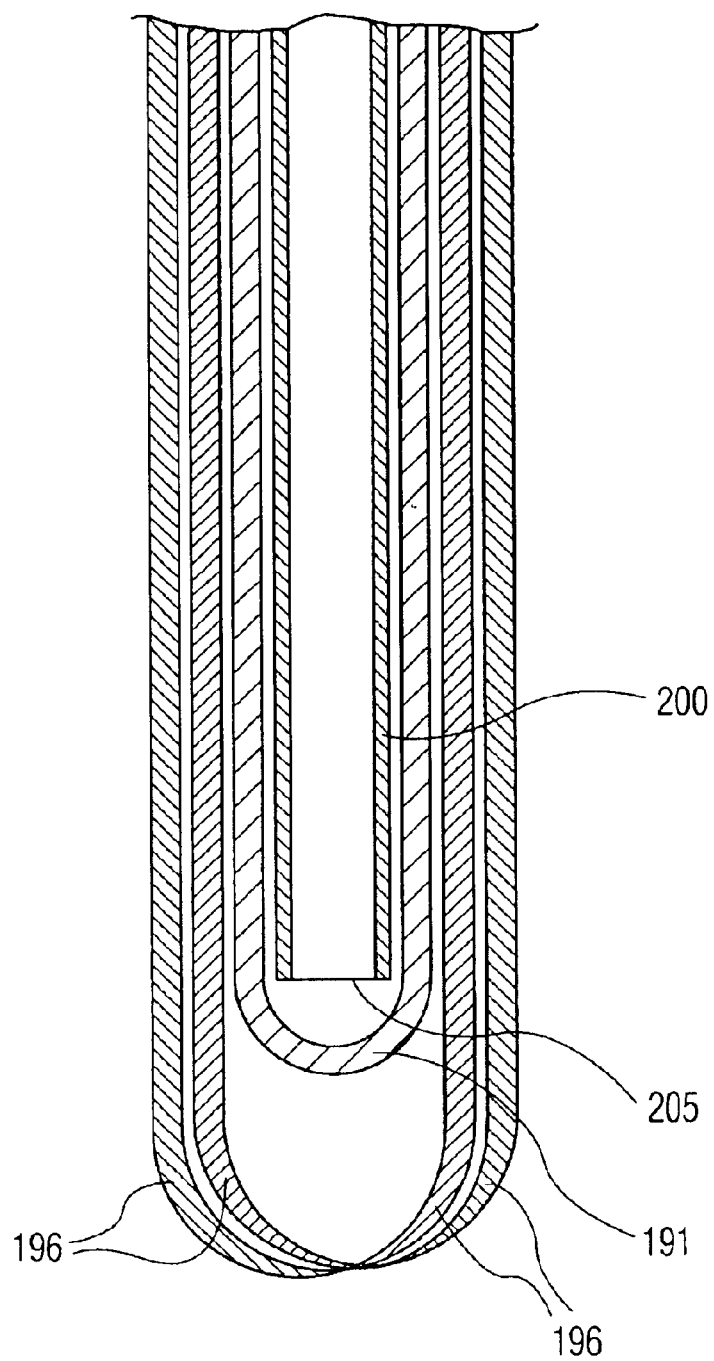
FIG. 20 illustrates a close-up, cross-sectional view of the inflatable balloon in accordance with the present invention.

FIG. 20 illustrates a close-up, partially cross sectional view of inflation balloon 191 within hemostatic fabric 196. Within inflation balloon 191 is internal inflation tube 200. Internal inflation tube 200 as shown in FIG. 20 is either an integral extension of an inflation tube 195 as seen in FIG. 19, or is a separate piece of tubing in fluid communication with an inflation tube 195 as seen in FIG. 19. Internal inflation tube 200 is shown as open at its end 205 in FIG. 20.

In FIG. 20, the hemostatic fabric 196 is shown folded back over itself along the length of the inflation balloon 191. In assembling the fabric tube 196 over the balloon 191, half the fabric length is first placed over the balloon and the excess fabric is given a complete turn (or 360° twist) before inverting the twisted excess fabric over the balloon the give the second layer of fabric. This has the effect of closing the fabric over the distal end of the balloon as shown in FIG. 20.

Figure 21:
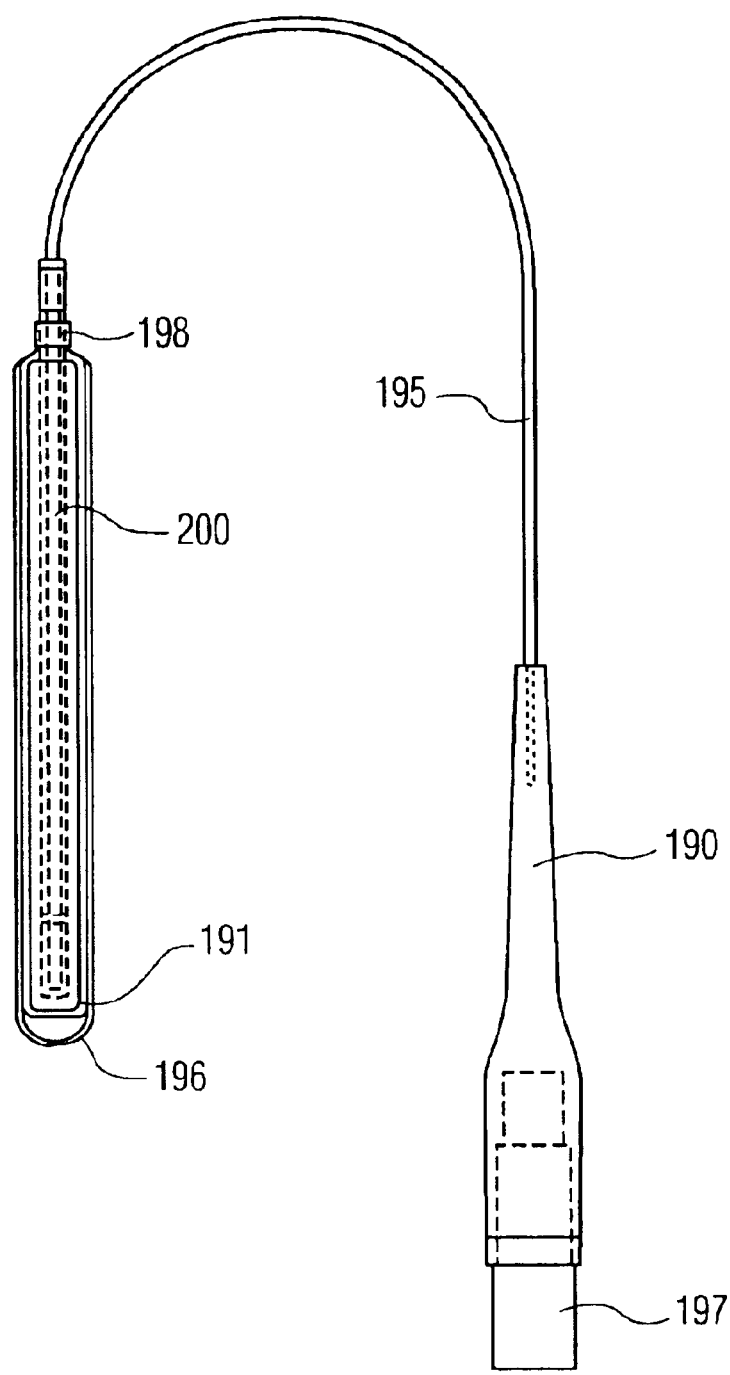
FIG. 21 illustrates the same embodiment as illustrated in FIG. 19 with the pilot balloon deflated and turned 90°.
Figure 22:
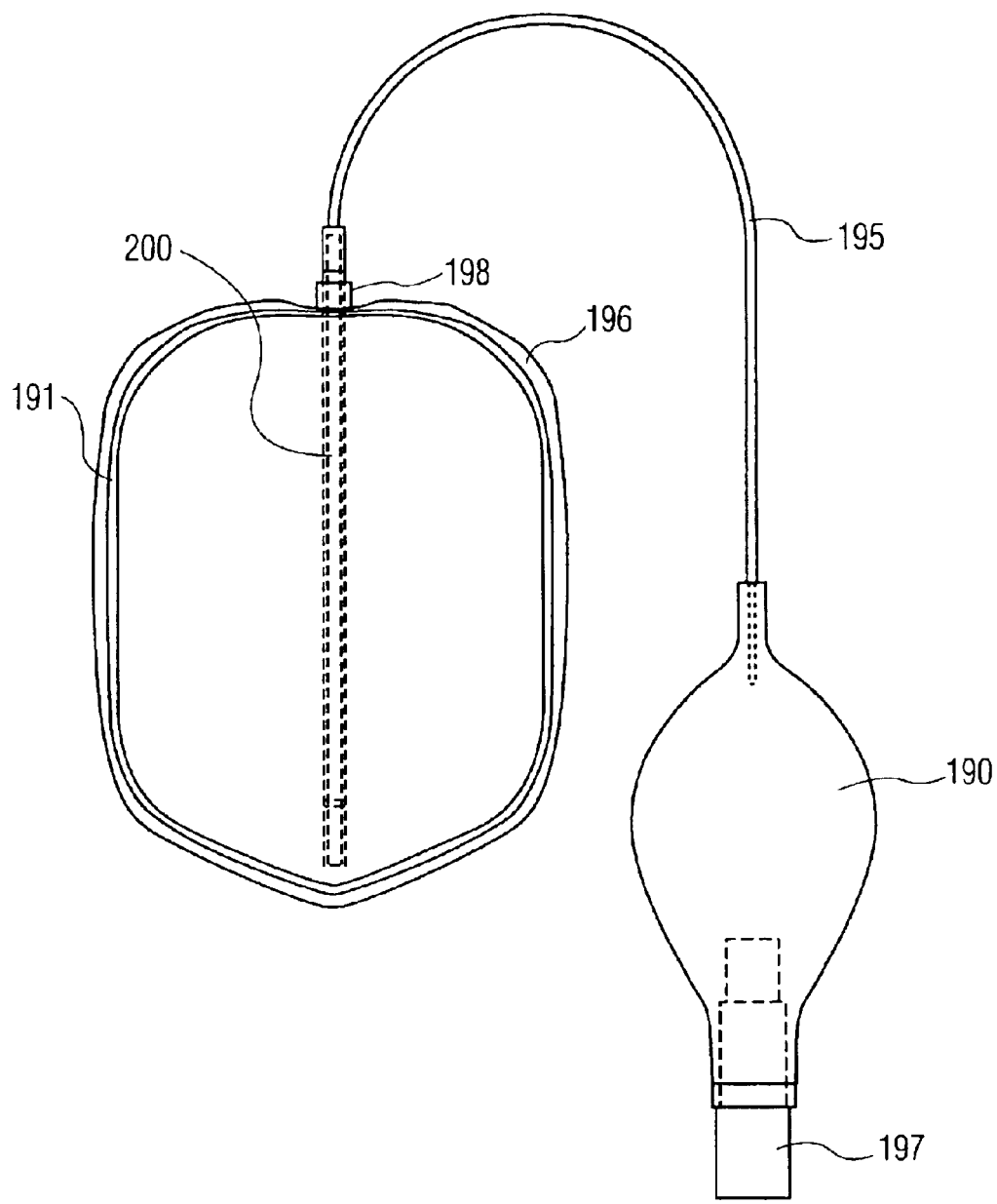
FIG. 22 illustrates the same embodiment as illustrated in FIG. 21 but with the system inflated.

FIG. 21 illustrates the embodiment shown in FIG. 19 with pilot balloon 190 turned 90° from the view shown in FIG. 19. FIG. 20 is presented to illustrate the deflated pilot balloon which accompanies deflated inflatable balloon 191. After air is introduced into the system, the resultant configuration of pilot balloon 190 is shown in FIG. 22. This inflated pilot balloon 190, as shown in FIG. 22, when touched or gripped by the doctor using the device, qualitatively indicates the pressure in the system.

In one embodiment, the pilot balloon as illustrated in FIGS. 19–22, has a wall thickness of about 0.09 mm (0.0035 inches) and is comprised of polyvinyl chloride (PVC). Typically, the pilot balloon is approximately 0.5 to 2 inches in length.

In its nasal embodiments, the method comprises the steps of inserting into a nasal cavity a first inflatable balloon surrounded at least in part by a hemostatic shroud comprising a gel-forming absorbent composition. The inflatable balloon is then expanded which compresses the shroud against the inner surface of the cavity where bleeding is to be controlled. Where the device includes a pilot balloon, the pressure inside the inflatable balloon is monitored, during expansion of the inflatable balloon and shroud, by touching the pressure-indicating pilot balloon which is in fluid communication with the first inflatable balloon.

7. One Embodiment of Plugging a Cavity

The complete procedure for plugging a cavity is carried out endoscopically. A preliminary examination is usually carried out in order to determine the extent of any bleeding or disease. In the specific case of diverticula, an preliminary examination would preferably include a combination of barium X-ray and colonoscopy. Such tests would determine the number and approximate position of the diverticula to be filled. Patient preparation is the same as for normal colonoscopy. Generally, the endoscope is inserted and the colon inflated.

A. Pre-Surgical Preparation

As shown in FIGS. 11 through 13, balloon 1 is mounted onto injection means 20 at the distal end of inner tube 21 with outer tube 22 or sheath 26 constraining the balloon within the recess (18 and 27, respectively). If the balloon includes an anchor 10, the anchor is folded, usually longitudinally along the balloon, and the balloon is mounted on the injection means, as shown in FIG. 11.

Air is removed from the apparatus before commencing the surgical operation by connecting the syringe (typically a 30 ml syringe, although a 20 ml syringe would also work) to stopcock 28a of luer fitting 28, opening stopcock 28a, and withdrawing the syringe piston. The stopcock is closed and the syringe removed. The apparatus is now ready for use.

B. Surgical Procedure

For a standard sized balloon, as shown in FIGS. 11 and 12, the user checks that the balloon 1, having hemostatic net 14 or hemostatic knitted textile material 15, is constrained within recess 18 and protected by outer tube 22 of catheter 17. The "Toughy-Borst" connector is tightened and the distal end of double walled catheter 17 is threaded through the working channel of a standard endoscope, the endoscope inserted, the colon inflated, and the balloon delivered to the mouth of a cavity using the controllable tip of the endoscope.

Figure 18:
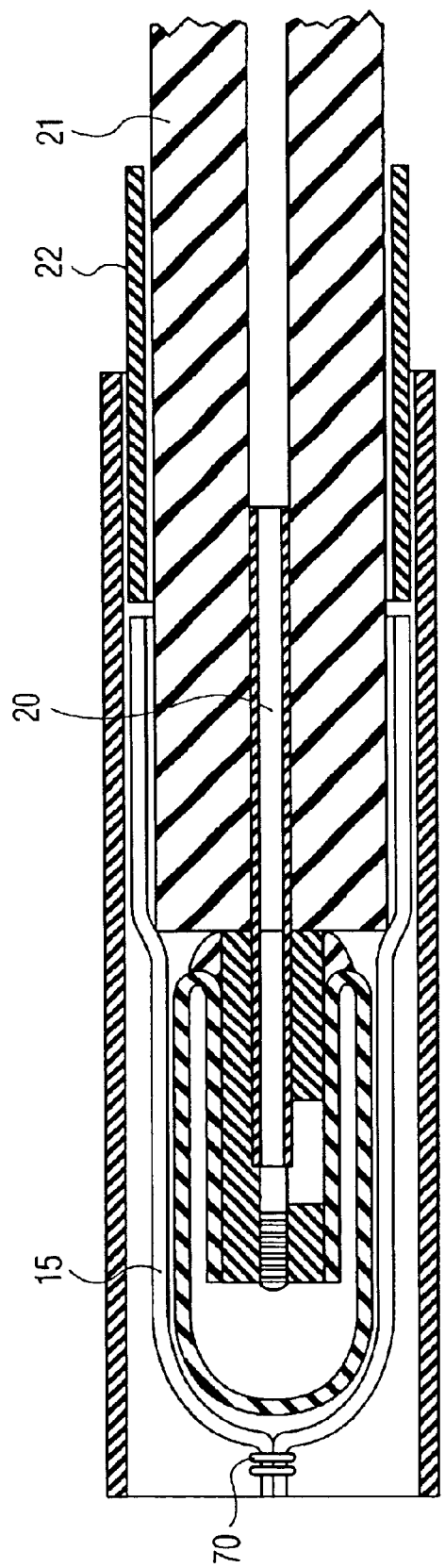
FIG. 18 illustrates an alternative embodiment of the invention with the sheath tied at one end.

FIG. 18 shows an alternative embodiment of hemostatic knitted textile material 15. In FIG. 18, hemostatic material 15 is tied at one end with a tying material 70. This is done to facilitate making hemostatic shrouds. The textile material is formed in long cylindrical tubes and cut to the desired length. Then, one end is tied with suitable thread to close the end. Suitable threads would be known by one skilled in the art. Other tying materials, other than thread, could also be used.

Prior to inserting balloon 1 into the cavity, it may be necessary to wash the inside of the cavity. In the specific case of diverticula, it may be necessary to wash them out prior to the balloon procedure. This can be carried out by placing the distal end of the outer tube over the mouth of the cavity, or diverticulum, and passing a bio-compatible fluid, such as water, through the inlet port on the "Toughy-Borst" type seal.

The distal end of the outer tube is presented to the mouth of the cavity and the balloon is pushed into said cavity by advancing inner tube 21.

After balloon 1 has been completely inserted into the cavity, a pressure controlled inflation device, preferably a 5 ml syringe containing sterile water with no air bubbles and fitted with a pressure gauge, is attached to stopcock 28a of standard luer fitting 28. The stopcock is opened and the balloon is filled so that the balloon completely fills the interior of the cavity. The required volume/pressure for inflation of the balloon can be determined by routine trial and error testing by a skilled person. It is desirable that the pressure does not exceed 65 kPa (10 psi), and more desirable that the pressure does not exceed 80 kPa, as leakage at the balloon and catheter junction may occur if too much pressure is applied or if the balloon is inflated too quickly. It is exemplary that the inner tube of the delivery device has a total volume of 1 ml and the balloon expands by 1 cm in diameter when filled with 0.53 ml of fluid.

Inner tube 21 is then withdrawn to remove injection means 20 from the inlet port of balloon 1 and non-return valve 4 prevents the water from escaping from the balloon. In other words, the filled balloon becomes resistant to deflation. The advantage of withdrawing the inner tube prior to withdrawing the outer tube is that the outer tube acts as a restraining brace, thereby preventing any undue force inside the cavity.

Figure 10:
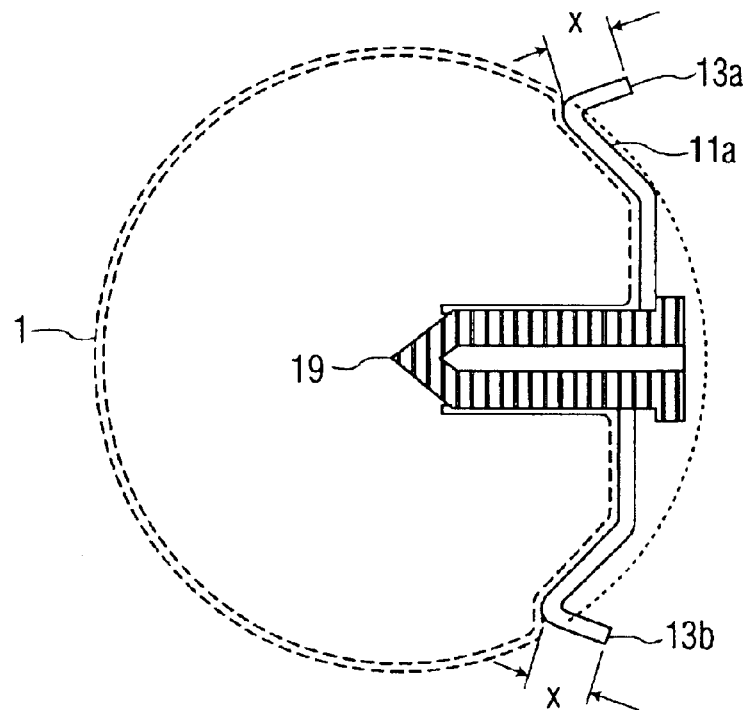
FIG. 10 is a longitudinal cross-sectional view of the balloon of FIG.7 inflated inside a diverticulum.

When balloon 1 and anchor 10 are inserted into a cavity and the balloon inflated, as shown in FIG. 10, the anchor returns to its retaining position in which the barbs 13a and 13b engage the interior wall of said cavity and prevent the balloon from being expelled. In the specific case of diverticula, the strong peristaltic movement of the bowel would tend to cause filler material to be expelled. The barbs of the anchor are arranged so that their penetration of a cavity interior wall is limited to the distance X. Herein, such arrangement to limit penetration is termed "abutment means."

In the alternative embodiment provided with anchor means, when a large diameter balloon or a balloon having a thicker hemostatic net 14 or a thicker hemostatic knitted material 15 is used, as shown in FIG. 13, the protective sheath 26 is moved towards the proximal end of double-walled catheter 17 to expose the top, preferably 3–4 mm, of balloon 1. The "Toughy-Borst" connector is tightened and the tip of the balloon is inserted into the mouth of a standard endoscope and double-walled catheter (17), generally with a first length of at least 75 mm, is pushed through sheath 26 and threaded through the working channel of the endoscope. Sheath 26 is withdrawn along the length of catheter 17 to the proximal end thereof. The remainder of the catheter is threaded through the channel of the endoscope, the endoscope inserted, the colon inflated, and the balloon delivered to the mouth of a cavity using the controllable tip of the endoscope.

The balloon is pushed into the cavity by advancing the inner tube. After the balloon has been completely inserted, it is inflated by the same procedure as described previously.

As a final step in the plugging procedure, the cavity which has been filled is marked by passing a dye spray down through the inlet port of the "Toughy-Borst" seal.

Once a cavity has been plugged with a balloon, the apparatus is reloaded with a separate balloon and the procedure is repeated as required. Hence, the balloon of the apparatus of the invention remains inside the patient and can therefore be said to be consumed in the treatment method since it is not available for any subsequent uses.

8. Alternative Filling Material

Curable Filler Material

Curable filler material is provided as a non-solid form (e.g., liquid, gel, or paste) and will cure or set to a solid form after insertion into a cavity. Generally, the material should set very quickly, so that the plugging procedure can proceed quickly.

Non-exhaustive examples of curable material include silicone elastomers, polyurethane foams and elastomers, epoxy resins, etc.

The skilled person will appreciate that curable materials can be provided in the form of two or more discrete substances which cure upon mixing. The mixing can be done upon delivery and insertion in the cavity.

Curing may be effected by a variety of means including solvent evaporation, UV or visible light irradiation, or heating. For example, the curable material cures at human body temperature.

Fibrous Filler Material

Fibrous filler material such as textile fibers or threads can be used to fill a cavity. Additionally, the fiber or thread can be coated with an adhesive material before or after insertion into said cavity.

Resiliently Deformable Member

Filling material in the form of a resiliently deformable member represents an alternative embodiment of the invention.

In use, the member is deformed from a retaining position into a second smaller position and inserted into a cavity. Once inside said cavity, the deformable member returns to its retaining position so that it is retained within said cavity.

In one embodiment, the deformable member is an elastomeric member (e.g., foamed plastic such as foamed silicone or foamed polyurethane) which can be compressed and inserted into a cavity. When the compression force is released, the member expands into its uncompressed retaining position and thereby fills said cavity.

The deformable member may also comprise a member formed from a shape memory alloy such as nitinol, which can be folded for insertion and expanded to a predetermined retaining position in response to a patient's body heat, for example.

9. Alternative Delivery Means

It should be appreciated that it may be necessary to use different delivery means depending on the filling material chosen to fill a body cavity.

If curable or fibrous filler material are used in combination with an anchor apparatus, the delivery device will comprise a two-part system—one for delivering the anchor and the other for delivering the filling material. A plurality of anchors can be mounted in a magazine at the distal end of the catheter.

The catheter allows the anchors to be fed one at a time into a delivery nozzle at the distal end. The delivery nozzle can be withdrawn to release the anchor, after the distal end of the catheter is placed into the neck of the body cavity. In this way, a number of anchors may be inserted into multiple diverticula without the need to withdraw the catheter from the endoscope after each insertion.

The filler material is injected into the diverticula using an injection catheter and syringe.

The catheter is multi-luminal when using a two-part mix which is curable upon actual mixing of the individual components. The two lumen come together at the distal end of the catheter and terminate into a single nozzle where the contents of each lumen are mixed. At the proximal end, the material is injected via a two lumen syringe.

According to the type of filler material used, curing can be carried out via another lumen of the injection catheter, or by a separate catheter. For example, a fibre optic carrying UV or visible light could be delivered via a separate lumen.

Delivery Catheter—Anchor

As shown in FIGS. 16a and 16b, a separate anchor delivery catheter may consist of an anchor ejector tube 31 and a central lumen 32 for spraying or injecting a marker dye. A number of folded anchors can be loaded into the distal end of the outer tube 33.

At the proximal end of the catheter is a mechanism which can withdraw the outer tube over the anchor ejector tube by an indexed amount equal to the length of one folded anchor.

The distal end of the catheter is inserted into the neck of the cavity and then the outer tube is withdrawn by an indexed amount. This will release one anchor into the cavity, allowing it to expand to its full size. In a particular embodiment, a flag is attached to the proximal end of the folded anchor, and is folded behind it. Thus, the flag will protrude from the neck of the cavity being treated.

Delivery Catheter—Filler

The design of the filler catheter varies according to the material type of the filler. In its simplest form, it is a single lumen tube with an injection nozzle at the distal end. The filler material is injected into the cavity by an indexing pump at the proximal end of the catheter.

If the filler material is a two part resin, then a bi-luminal catheter is used with a mixer nozzle at the distal end.

10. Other Methods: Using a Separate Anchor and Non-Solid Curable and/or Fibrous Filler Materials According to an embodiment of the invention, the first part of the procedure is to insert the anchors. The loaded insertion catheter is first introduced into the colon via the working lumen of the endoscope. These are inserted into the cavity from an anchor magazine insertion arrangement on the distal end of the insertion catheter. Soluble or biodegradable flags may be left protruding from the cavity neck to indicate which have had an anchor apparatus inserted.

When all the anchors have been inserted, the anchor insertion catheter is withdrawn from the endoscope.

As an alternative to the flag, a central lumen of the anchor insertion catheter may be used to spray a dye around the neck of the filled cavity. To prevent the dye from leaking proximally, the proximal end of the outer tube is terminated in a seal of the "Toughy-Borst" type.

The filler catheter is now introduced into the colon via the endoscope lumen. Using the flags (or dye spray) as a guide, each cavity is injected with the filler material, so that it is completely filled. The material will be in the form of a gel, or a glue coated textile fiber, so that it will not be expelled from the cavity before it is cured.

If the filler material is self-curing, then all that remains is to leave the colon inflated until the material is set. If the material requires an additional curing means, then such additional means are subsequently applied.

The foregoing comprises a description of certain exemplary embodiments of the present invention. The invention is not limited to these embodiments, however, and the subjoined claims are intended to be construed to encompass all embodiments of this invention, and equivalents and variants thereof, which may be made by those skilled in the art without departing from the true spirit and scope of the essential concepts disclosed and claimed herein.

What is claimed:

1. A method for controlling bleeding on an inner wall of a body cavity or passageway comprising:
    inserting into said cavity a first expandable balloon surrounded at least in part by a hemostatic shroud comprised of a fabric and a gel-forming absorbent composition, said first expandable balloon fluidly connected to an expandable pilot balloon;
    inflating said first expandable balloon therein;
    compressing said shroud against said inner surface of the cavity where bleeding is to be controlled; and
    monitoring the pressure within said first expandable balloon by touching said expandable pilot balloon.

2. The method of claim 1 further comprising the step of deflating said first expandable balloon after said shroud is compressed against said inner surface of said cavity.

3. The method of claim 2 further comprising the step of removing said first expandable balloon and said shroud after the step of deflating said first expandable balloon.

4. The method of claim 1 wherein said first expandable balloon is inflatable but non-stretchable.

5. The method of claim 1 wherein said pilot balloon is inflatable but non-stretchable.

6. The method of claim 1 wherein said first expandable balloon is subsequently removed from said body cavity, leaving said shroud in contact with said inner surface.

7. A device for controlling bleeding in a body cavity, said device comprising:
    a first expandable balloon having an inner and outer surface;
    an expandable pilot balloon; and
    a hemostatic shroud;
    said shroud surrounding at least part of said outer surface of said first expandable balloon and comprising a gel-forming absorbent composition;
    said first expandable balloon and shroud having a configuration adapted to permit insertion thereof into a body cavity wherein bleeding is to be controlled and, upon said insertion, inflation of said first expandable balloon to occupy said cavity and to press said shroud against the inner wall of said cavity;
    said expandable pilot balloon and said first expandable balloon in fluid communication with each other such that the pressure inside said expandable pilot balloon equals the pressure inside said first expandable balloon.

8. The device of claim 7 wherein said hemostatic shroud is permanently affixed to the delivery means in such a way that said shroud is permanently positioned around said first expandable balloon.

9. The device of claim 7 wherein said hemostatic shroud is releasably affixed to said first expandable balloon.

10. The device of claim 7 further comprising a catheter to insert and inflate said first expandable balloon, said catheter comprising a catheter tube having an inner lumen, a wall, two ends, and an inflation passageway disposed within said wall.

11. The device of claim 10 wherein said first expandable balloon is disposed on said balloon catheter tube.

12. The device of claim 11 wherein said first expandable balloon is affixed to the outer surface of said catheter tube at the two ends of said catheter tube, and wherein said inflation passageway disposed within said wall of said tube terminates at said outer surface of said catheter tube.

13. The device of claim 11 wherein said first inflatable, non-stretchable balloon is configured for insertion into a nasal passageway and the inner lumen of said tube serves as an air passage for breathing.

14. The device of claim 7 wherein said hemostatic shroud is comprised of a material selected from a group consisting of hemostatic polysaccharides, oxidized cellulose, carboxymethylcellulose (CMC), and calcium alginate.

15. The device of claim 7 wherein the hemostatic shroud is in the form of a knitted fabric tube.

16. The device of claim 7 further comprising an extension tail on said hemostatic shroud.

17. The device of claim 7 further comprising an inflation tube disposed between said expandable pilot balloon and said first expandable balloon.

18. A method for controlling bleeding on an inner wall of a body cavity or passageway comprising:
    inserting into said cavity a first inflatable, non-stretchable balloon surrounded at least in part by a hemostatic shroud comprised of a fabric and a gel-forming absorbent composition, said first inflatable, non-stretchable balloon fluidly connected to an inflatable, non-stretchable pilot balloon;

inflating said first inflatable, non-stretchable balloon therein;

compressing said shroud against said inner surface of the cavity where bleeding is to be controlled; and monitoring the pressure within said first inflatable, non-stretchable balloon by touching said inflatable, non-stretchable pilot balloon.

19. The method of claim 18 further comprising the step of deflating said first inflatable, non-stretchable balloon after said shroud is compressed against said inner surface of said cavity.

20. The method of claim 19 further comprising the step of removing said inflatable, non-stretchable balloon after the step of deflating said balloon.

21. The method of claim 18 wherein said gel-forming absorbent composition provides a non-stick layer between said fabric and said inner surface of said cavity.

22. The method of claim 18 wherein said first inflatable, non-stretchable balloon is subsequently removed from said body cavity, leaving said shroud in contact with said inner surface.

23. The method of claim 18 wherein said shroud is removable after being in contact with said inner surface.

24. The method of claim 18 wherein said shroud is releasably affixed to said first inflatable, non-stretchable balloon.

25. The method of claim 18 wherein said first inflatable, non-stretchable balloon is inflated by a balloon catheter, said balloon catheter having a catheter tube which has an outer wall and an inner lumen.

26. The method of claim 25 wherein said first inflatable, non-stretchable balloon is disposed on said catheter tube.

27. The method of claim 26 wherein said first inflatable, non-stretchable balloon is inflated through an inflation port which is disposed in the wall of said catheter tube.

28. The method of claim 25 wherein said first inflatable, non-stretchable balloon is configured for insertion into a nasal passageway and the inner lumen of said catheter tube serves as an air passage for breathing.

29. The method of claim 19 wherein said hemostatic shroud has an extension tail which facilitates removal of the hemostatic shroud after said first inflatable, non-stretchable balloon has been deflated.

30. The method of claim 18 wherein said pressure-monitoring step is performed during the compression of said shroud.

31. A device for controlling bleeding in a body cavity, said device comprising:

a first inflatable, non-stretchable balloon having an inner and outer surface;

an inflatable, non-stretchable pilot balloon; and a hemostatic shroud;

said shroud surrounding at least part of said outer surface of said first inflatable, non-stretchable balloon and comprising a gel-forming absorbent composition;

said first inflatable, non-stretchable balloon and shroud having a configuration adapted to permit insertion thereof into a body cavity wherein bleeding is to be controlled and, upon said insertion, inflation of said first inflatable, non-stretchable balloon to occupy said cavity and to press said shroud against the inner wall of said cavity;

said inflatable, non-stretchable pilot balloon and said first inflatable, non-stretchable balloon in fluid communication with each other such that the pressure inside said inflatable, non-stretchable pilot balloon equals the pressure inside said first inflatable, non-stretchable balloon.

32. The device of claim 31 wherein said hemostatic shroud is releasably affixed to said first expandable balloon.

33. The device of claim 31 further comprising a catheter to insert and inflate said first inflatable, non-stretchable balloon, said catheter comprising a catheter tube having an inner lumen, a wall, two ends, and an inflation passageway disposed within said wall.

34. The device of claim 31 wherein said first inflatable, non-stretchable balloon is disposed on said balloon catheter tube.

35. The device of claim 34 wherein said first inflatable, non-stretchable balloon is affixed to the outer surface of said catheter tube at the two ends of said catheter tube, and wherein said inflation passageway disposed within said wall of said tube terminates at said outer surface of said catheter tube.

36. The device of claim 35 wherein said first inflatable, non-stretchable balloon is configured for insertion into a nasal passageway and the inner lumen of said tube serves as an air passage for breathing.

37. The device of claim 31 wherein said hemostatic shroud is comprised of a material having the property of facilitating blood clot formation.

38. The device of claim 37 wherein said hemostatic shroud is comprised of a material selected from a group consisting of hemostatic polysaccharides, oxidized cellulose, carboxymethylcellulose (CMC), and calcium alginate.

39. The device of claim 31 wherein the hemostatic shroud is in the form of a knitted fabric tube.

40. The device of claim 31 further comprising an extension tail on said hemostatic shroud.

41. The device of claim 31 further comprising an extension tail on said hemostatic shroud.

* * * * *